(12) United States Patent
Hartman et al.

(10) Patent No.: US 7,265,134 B2
(45) Date of Patent: Sep. 4, 2007

(54) TYROSINE KINASE INHIBITORS

(75) Inventors: George D. Hartman, Lansdale, PA (US); Thomas J. Tucker, North Wales, PA (US); John T. Sisko, Lansdale, PA (US); Anthony M. Smith, Green Lane, PA (US); William C. Lumma, Jr., Helena, MO (US)

(73) Assignee: Merck & Co., Inc., Rahway, NJ (US)

( * ) Notice: Subject to any disclaimer, the term of this patent is extended or adjusted under 35 U.S.C. 154(b) by 506 days.

(21) Appl. No.: 10/486,574

(22) PCT Filed: Aug. 13, 2002

(86) PCT No.: PCT/US02/27156

§ 371 (c)(1),
(2), (4) Date: Feb. 11, 2004

(87) PCT Pub. No.: WO03/015778

PCT Pub. Date: Feb. 27, 2003

(65) Prior Publication Data

US 2004/0192926 A1    Sep. 30, 2004

Related U.S. Application Data

(60) Provisional application No. 60/313,234, filed on Aug. 17, 2001.

(51) Int. Cl.
*A61K 31/426* (2006.01)
*A61K 31/4535* (2006.01)
*C07D 417/12* (2006.01)
*C07D 401/12* (2006.01)
*C07D 277/38* (2006.01)

(52) U.S. Cl. ............... 514/326; 514/254.02; 514/370; 546/209; 544/369; 548/190

(58) Field of Classification Search ............... 546/198, 546/197, 209; 514/326, 254.02, 370; 544/369; 548/190
See application file for complete search history.

(56) References Cited

U.S. PATENT DOCUMENTS

| 3,734,923 A | 5/1973 | Dowding et al. |
| 3,755,347 A | 8/1973 | Guillot et al. |
| 6,596,746 B1 * | 7/2003 | Das et al. ............ 514/370 |

FOREIGN PATENT DOCUMENTS

| CH | 451 156 | 5/1968 |
| EP | 0 069 784 A1 | 5/1982 |
| EP | 0 069 784 B1 | 12/1987 |
| EP | 0 928 790 A1 | 7/1999 |
| FR | 7.428 M | 12/1969 |
| FR | 2 252 808 | 6/1975 |
| WO | WO95 09852 A1 | 4/1995 |
| WO | WO99 62890 | 12/1999 |
| WO | WO 00 02871 A1 | 1/2000 |
| WO | WO 00 26203 A1 | 5/2000 |
| WO | WO 01 17995 A1 | 3/2001 |
| WO | WO 02 45652 A2 | 6/2002 |
| WO | WO 03 000687 A1 | 1/2003 |
| WO | WO 03 015717 | 2/2003 |

OTHER PUBLICATIONS

Obach R.S., Drug-drug interactions; An important negative attribute in drugs, Durgs of Today, 39(5), 301-38, (2003).*
Diabetic Retinopathy [online], [retrieved on Nov. 16, 2006]. Retrieved from the Internet, URL: http:http://www.nei.nih.gov/health/diabetic/retinopathy.asp.*
Golub et al, Oct. 15, 1999, Science, 286, 531-537.*
Hortobagyi, G., Oct. 1, 1998, N Engl J Med, 339, 974-984.*
Drack, Preventing Blindness in Premature Infants, May 28, 1998, N. Engl. J. Med, 338(22), 1619-1621.*
Lee et al, Brain tissue responses to ischemia, Sep. 2000, Journal of Clinical Investigation, 106(6), 723-731.*
J. Rak et al. Cancer Research, 55:4575-4580, 1995.
G. Gasparini and A.L. Harris, J. Clin. Oncol., 1995, 13:765-782.
M. Toi et al., Japan. J. Cancer Res., 1994, 85:1045-1049.
A.J. Dickinson et al., Br. J. Urol., 1994, 74:762-766.
L.M. Ellis et al., Surgery, 1996, 120(5):871-878.
J.K. Williams et al., Am. J. Surg., 1994, 168:373-380.
A. Amirkhosravi et al., Platelets, 10:285-292 (1999).
S.P. Gunningham, et al., Can. Research, 61: 3206-3211 (2001).
A. Giatromanolaki et al., J. Pathol. 2001; 194:101-108.
Michael Detmar, J. Dermatological Sci., 24 Suppl. 1, S78-S84 (2000).
Hasegawa et al., Skeletal Radiol., vol. 28, pp. 41-45, 1999.
Brockelsby et al., Laboratory Investigation 79:1101-1111 (Sep. 1999).
Paul et al., Nature Med 7:222-227 (2001).
Matsuyama et al., J. Neurol. Sci. 186:75-79 (2001).

(Continued)

*Primary Examiner*—Kamal A. Saeed
*Assistant Examiner*—Karen Cheng
(74) *Attorney, Agent, or Firm*—Nicole M. Beeler; David A. Muthard

(57) ABSTRACT

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

5 Claims, No Drawings

OTHER PUBLICATIONS van der Flier et al., J. Infectious Diseases, 183:149-153 (2001).
Stephen K. Smith, Trends in Endocrinology & Metabolism, vol. 12, No. 4, pp. 147-151, May/Jun. 2001.
Levis et al., Blood, vol. 98, No. 3, pp. 885-887 (2001).
Rajesh K. Jain, Nature Medicine, vol. 7. No. 9, pp. 987-989 (Sep. 2001).
Giulio Jori, Lasers Med. Sci., 1990; 5: 115-120.
Chuannong Zhou, J. Photochem. and Photobiol. 1989; 3: 299-318.
Hendrich et al., Knee Surg Sports Traumatol Arthroscopy 5: 58-63 (1997).
Hall et al., Am J Hum Genet 61:785-789, 1997.
Li et al., Gene Therapy, 1998; 5:1105-13.
Fathallah-Shaykh et al., J Immunol 2000; 164:217-222.
Dougherty et al., J. Natl. Cancer Inst., 1998, 90(12): 889-905.
Van Bruggen et al., J. Clin. Invest,. 104:1613-1620 (1999).
Gerber et al., Nature Medicine, vol. 5, No. 6, pp. 623-628, 1999.
David A. Greenberg, Drug News Perspect 11(5):265-270 (1998).
Nakagawa et al., FEBS Let. 473:161-164 (2000).
Peter Traxler, Exp. Opin. Ther. Patents 8 (12) 1599-1625(1998).
Peter M. Traxler, Exp. Opin. Ther. Patents 7(6) 571-588 (1997).
Joseph V. Simone, Cecil Textbook of Medicine 20th Edition, vol. 1, pp. 1004-1010 (1996).
Lawrence et al., Pub Med Abstract, vol. 77(2), pp. 81-114 (1998).
Cuckler, et al., Nithiazide I. Chemical and Biological Studies, vol. 92, pp. 483-488 (1956).
Nagano, et al., Studies on Organic Sulfur Compounds, vol. 21, pp. 2408-2416 (1973).
Werbel, et al., Journal of Medicinal Chemistry, vol. 15, No. 9 pp. 955-963 (1972).
Micich, et al., Journal of the American Oil Chemists' Society, vol. 59, No. 10 pp. 448-452 (1982).

* cited by examiner

TYROSINE KINASE INHIBITORS

PRIORITY CLAIM

This application is a §371 application of PCT/US02/27156 that was filed on Aug. 13, 2002, which claims priority from the U.S. Provisional Application No. 60/313,234, that was filed on Aug. 17, 2001 and is now abandoned.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

The following is provided as background information only and should not be taken as an admission that any subject matter discussed or that any reference mentioned is prior art to the instant invention Tyrosine kinases are a class of enzymes that catalyze the transfer of the terminal phosphate of adenosine triphosphate to tyrosine residues in protein substrates. They play critical roles in signal transduction for a number of cell functions via substrate phosphorylation. Though the exact mechanism of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. Then there is the FLK family which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6):334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene*, 8:2025-2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, *J. Cell Biol.* 129:895-898, 1995). One such receptor-type tyrosine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11-15, 1993). VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, *Cytokine & Growth Factor Reviews* 7:259-270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841-844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti- VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1-8, 1991).

Accordingly, the identification of small compounds which specifically inhibit, regulate and/or modulate the signal transduction of tyrosine kinases is desirable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts and stereoisomers thereof:

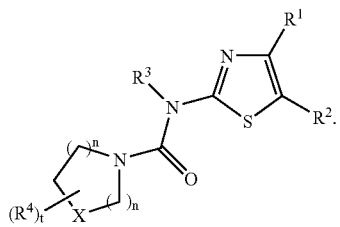

I

DETAILED DESCRIPTION OF THE INVENTION

The compounds of this invention are useful in the inhibition of kinases and are illustrated by a compound of Formula I:

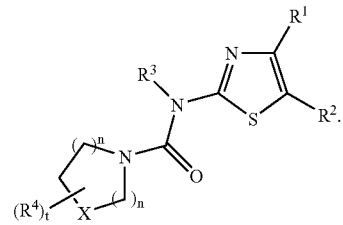

I or a pharmaceutically acceptable salt or stereoisomer thereof, wherein
X is: C—H or N—$R^{3a}$;
n is independently: 0, 1, or 2;
t is: 1 through 6;
$R^1$ is:
  1) H,
  2) halo,
  3) $C_{1-6}$ alkyl, or
  4) $OC_{1-6}$ alkyl;
$R^2$ is:
  1) aryl, optionally substituted with one to three substituents selected from:
    a) halo,
    b) $OC_{1-3}$ perfluoroalkyl,
    c) $OC_{1-6}$ alkyl,
    d) CN,
    e) OH,
    f) $SO_2R^d$,
    g) $C_{1-6}$alkyl,
    h) i) (C=O)$R^d$, and
    i) $CO_2R^d$,
  2) CN,
  3) (C=O)$NR^aR^b$,
  4) halo,
  5) $C_{3-6}$ cycloalkyl, or
  6) —C≡C—$R^c$;
$R^3$ is:
  1) H,
  2) $C_{1-8}$ alkyl,
  3) $SO_2R^d$,
  4) (C=O)$R^d$, or
  5) $CO_2R^d$;
$R^{3a}$ is:
  1) H,
  2) $SO_2R^d$,
  3) heterocyclyl,
  4) (C=O)$R^d$,
  5) $CO_2R^d$, or
  6) $C_{1-8}$ alkyl, said alkyl is optionally substituted with one to three substituents selected from oxo, heterocyclyl, halo, $NR^5R^6$, $CO_2H$, $CO_2R^d$, $CONR^5R^6$, OH and $OC_{1-6}$ alkyl;
$R^4$ is:
  1) H,
  2) $C_{0-6}$ alkylene-$NR^5R^6$,
  3) $CO_2H$,
  4) $CO_2R^d$,
  5) halo,
  6) OH,
  7) $C_{1-8}$ alkoxy, or 8) $C_{1-8}$ alkyl, said alkyl is optionally substituted with one to three substituents selected from oxo, heterocylcyl, halo, $NR^5R^6$, $CO_2H$, $CO_2R^d$, $CONR^5R^6$, OH and $OC_{1-6}$ alkyl;

$R^5$ and $R^6$ are independently:
1) H,
2) $C_{1-8}$ alkyl,
3) $SO_2R^d$,
4) $CO_2R^d$,
5) $(C=O)R^d$,
6) $C_{1-8}$ alkylene-$NR^aR^b$,
7) $C_{1-8}$ alkylene-$(CO)NR^aR^b$,
8) $C_{1-8}$ alkylene-heterocyclyl, or
9) aryl, said aryl and heterocyclyl optionally substituted with one or more substituents selected from $C_{1-6}$ alkyl, $C_{1-3}$ perfluoroalkyl, $C_{1-6}$ alkoxy, $OCF_3$, $SO_2R^d$, $NR^aR_b$ and halo; or $R^5$ and $R^6$ are taken with the nitrogen to which they are attached to form a monocyclic or bicyclic heterocycle with 5-7 members in each ring, said heterocycle optionally substituted with one or more substituents selected from halo, $C_{1-6}$ alkyl, $OC_{1-6}$ alkyl, $OCF_3$, $CO_2R^d$, $(C=O)R^d$, aryl, heterocyclyl, $SO_2R^d$ and OH;

$R^a$ and $R^b$ are independently:
1) H,
2) $C_{1-6}$ alkyl,
3) $C_{3-6}$ cycloalkyl,
4) phenyl,
5) $CO_2R^d$,
6) $(C=O)R^d$, or
7) $SO_2R^d$;

$R^c$ is H, phenyl, or $C_{1-6}$ alkyl; and
$R^d$ is phenyl or $C_{1-6}$ alkyl.

A second embodiment is illustrated by the compound described above, or a pharmaceutically acceptable salt or stereoisomer thereof, wherein $R^2$ is:
1) phenyl, optionally substituted with one or two substituents selected from:
   a) halo,
   b) $OC_{1-3}$ perfluoroalkyl,
   c) $OC_{1-6}$ alkyl,
   d) CN, and
   e) $C_{1-6}$ alkyl,
2) CN,
3) $(C=O)NR^aR^b$, or
4) halo.

A third embodiment encompassed by the instant invention is a compound as described immediately above or a pharmaceutically acceptable salt or stereoisomer thereof, wherein n is independently 1 or 2.

Another embodiment is e compound of claim 3, or a pharmaceutically acceptable salt or stereoisomer thereof, wherein $R^1$, $R^3$, $R^4$ are H.

And yet another embodiment is a compound selected from:

N-(5-phenylthiazol-2-yl)-N'-[4-(2-pyridyl)piperazin-1-yl]urea;
N-(5-phenylthiazol-2-yl)-N'-[4-(2-pyrimidinyl)piperazin-1-yl]urea;
N-(5-phenylthiazol-2-yl)-N'-(4-aminopiperidin-1-yl)urea;
N-(5-phenylthiazol-2-yl)-N'-[4-(2-pyrimidinoxy)piperidin-1-yl)]urea;
N-(5-phenylthiazol-2-yl)-N'-(4-carboxypiperidin-1-yl)urea;
N-(5-phenylthiazol-2-yl)-N'-(3-carboxyazetidin-1-yl)urea;
N-(5-phenylthiazol-2-yl)-N'-[4-(pyrrolidinocarbonylmethyl)piperazine-1-yl]-urea; or a pharmaceutically acceptable salt or stereoisomer thereof.

And still another embodiment is a compound which is (5-phenylthiazol-2-yl)-N'-[4-(2-pyrimidinyl)piperazin-1-yl]urea or a pharmaceutically acceptable salt thereof.

A further embodiment is a compound which is N-(5-phenylthiazol-2-yl)-N'-(4-aminopiperidin-1-yl)urea or a pharmaceutically acceptable salt thereof.

And yet another embodiment is a compound which is N-(5-phenylthiazol-2-yl)-N'-(3-carboxyazetidin-1-yl)urea or a pharmaceutically acceptable salt thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Utilities

The instantly disclosed compounds are inhibitors of tyrosine kinase and are therefore useful to treat or prevent tyrosine kinase-dependent diseases or conditions in mammals.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like). In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention encompasses a method of treating or preventing cancer in a mammal in need of such treatment which is comprised of administering to said mammal a therapeutically effective amount of a compound of Formula I. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, glioblastomas and breast carcinoma. The utility of angiogenesis inhibitors in the treatment of cancer is known in the literature, see J. Rak et al. *Cancer Research*, 55:4575-4580, 1995, for example. The role of angiogenesis in cancer has been shown in numerous types of cancer and tissues: breast carcinoma (G. Gasparini and A. L. harris, *J. Clin. Oncol.*, 1995, 13:765-782; M. Toi et al., *Japan. J. Cancer Res.*, 1994, 85:1045-1049); bladder carcinomas (A. J. Dickinson et al., *Br. J. Urol.*, 1994, 74:762-766); colon carcinomas (L. M. Ellis et al., *Surgery*, 1996, 120(5):871-878); and oral cavity tumors (J. K. Williams et al., *Am. J. Surg.*, 1994, 168:373-380).

Tumors which have undergone neovascularization show an increased potential for metastasis. VEGF released from cancer cells enhances metastasis possibly by increasing extravasation at points of adhesion to vascular endothelium. (A. Amirkhosravi et al., *Platelets*, 10:285-292 (1999)). In fact, angiogenesis is essential for tumor growth and metastasis. (S. P. gunningham, et al., *Can. Research*, 61: 3206-3211 (2001)). The angiogenesis inhibitors disclosed in the present application are therefore also useful to prevent or decrease tumor cell metastasis. Such a use is also contemplated to be within the scope of the present invention.

Further included within the scope of the invention is a method of treating or preventing a disease in which angiogenesis is implicated, which is comprised of administering to a mammal in need of such treatment a therapeutically effective amount of a compound of Formula I. Ocular neovascular diseases are an example of conditions where much of the resulting tissue damage can be attributed to aberrant infiltration of blood vessels in the eye (see WO 00/30651, published 2 Jun. 2000). The undesireable infiltration can be triggered by ischemic retinopathy, such as that resulting from diabetic retinopathy, retinopathy of prematurity, retinal vein occlusions, etc., or by degenerative diseases, such as the choroidal neovascularization obeserved in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formula I. Examples of such inflammatory diseases are rheumatoid arthritis, psoriasis, contact dermatitis, delayed hypersensitivity reactions, and the like. (A. Giatromanolaki et al., *J. Pathol.* 2001; 194:101-108.) For the role of VEGF in skin angiogenesis, see Michael Detmar, *J. Dermatological Sci.*, 24 Suppl. 1, S78-S84 (2000).

Also included within the scope of the present invention is a method of treating or preventing bone associated pathologies selected from osteosarcoma, osteoarthritis, and rickets, also known as oncogenic osteomalacia. (Hasegawa et al., *Skeletal Radiol.*, 28, pp. 41-45, 1999; Gerber et al., *Nature Medicine*, Vol. 5, No. 6, pp. 623-628, June 1999.) And since VEGF directly promotes osteoclastic bone resorption through KDR/Flk-1 expressed in mature osteoclasts (FEBS Let. 473:161-164 (2000); *Endocrinology*, 141:1667 (2000)), the instant compounds are also useful to treat and prevent conditions related to bone resorption, such as osteoporosis and Paget's disease.

A method of treating or preventing preeclampsia is also within the which comprises administering a therapeutically effective amount of a compound of Formula I. Studies have shown that the action of VEGF on the Flt-1 receptor is pivotal in the pathogenesis of preeclampsia. (*Laboratory Investigation* 79:1101-1111 (September 1999).) Vessels of pregnant women incubated with VEGF exhibit a reduction in endothelium-dependent relaxation similar to that induced by plasma from women with preeclampsia. In the presence of an anti-Flt-1 receptor antibody, however, neither VEGF or plasma from women with preeclampsia reduced the endothelium-dependent relaxation. Therefore the claimed compounds serve to treat preeclampsia via their action on the tyrosine kinase domain of the Flt-1 receptor.

Also within the scope of the invention is a method of reducing or preventing tissue damage following a cerebral ischemic event which comprises administering a therapeutically effective amount of a compound of Formula I. The claimed compounds can also be used to reduce or prevent tissue damage which occurs after cerebral ischemic events, such as stroke, by reducing cerebral edema, tissue damage, and reperfusion injury following ischemia. (*Drug News Perspect.* 11:265-270 (1998); *J. Clin. Invest.* 104:1613-1620 (1999); *Nature Med.* 7:222-227 (2001)).

The instant compounds can also be used to prevent or treat tissue damage during bacterial meningitis, such as tuberculous meningitis. Matsuyama et al., *J. Neurol. Sci.* 186:75-79 (2001)). The instant invention therefore encompasses a method of treating or preventing tissue damage due to bacterial meningitis which comprises administering a therapeutically effective amount of a compound of Formula 1. Studies have shown that VEGF is secreted by inflammatory cells during bacterial meningitis and that VEGF contributes to blood-brain barrier disruption. (van der Flier et al., *J. Infectious Diseases*, 183:149-153 (2001)). The claimed compounds can inhibit VEGF-induced vascular permeability and therefore serve to prevent or treat blood-brain barrier disruption associated with bacterial meningitis.

The present invention further encompasses a method to treat or prevent endometrioses comprised of administering a therapeutically effective amount of a compound of Formula I. An increase in VEGF expression and angiogenesis is associated with the progression of endometriosis (Stephen K. Smith, *Trends in Endocrinology & Metabolism*, Vol. 12, No. 4, May/June 2001). Inhibition of VEGF by the current compounds would therefore inhibit angiogenesis and treat endometriosis.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The instant compounds are also useful in combination with known anti-cancer agents. Such known anti-cancer agents include the following: estrogen receptor modulators, androgen receptor modulators, retinoid receptor modulators, cytotoxic agents, antiproliferative agents, phenyl-protein transferase inhibitors, HMG-CoA reductase inhibitors, HIV protease inhibitors, reverse transcriptase inhibitors, and other angiogenesis inhibitors. The instant compounds are particularly useful when coadminsitered with radiation therapy. The synergistic effects of inhibiting VEGF in combination with radiation therapy have been described in the art (see WO 00/61186).

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, and BMS 188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-k1]acridine-2-(6H) propanamine, 1-amino-9-ethyl-5-fluoro-2,3-dihydro-9-hydroxy-4-methyl-1H,12H-benzo[de]pyrano[3',4':b,7] indolizinol[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexahydrofuro(3',4':6,7)naphtho(2,3-d)-1,3-dioxol-6one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indenol[2,1-c]quinolin-7-one, and dimesna.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplodine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

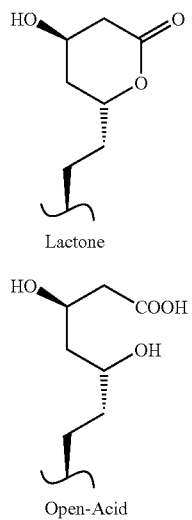

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl) methyl]-4-(3-chlorophenyl)1-methyl-2(1H)-quinolinone, (−)-6-[amino(4-chlorophenyl)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin- 5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p.573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p.107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Other examples of specific inhibitors of COX-2 include the following:

3-(3-fluorophenyl)-4-(4-(methylsulfonyl)phenyl)-2-(5H)-furanone;

3-(3,4-difluorophenyl)-4-(4-(methylsulfonyl)phenyl)-2-(5H)-furanone;

3-(3,4-dichlorophenyl)-4-(4-(methylsulfonyl)phenyl)-2-(5H)-furanone;

3-phenyl-4-(4-(methylsulfonyl)phenyl)-2-(5H)-furanone;

5,5-dimethyl-3-(3-fluorophenyl)-4-(4-methylsulfonyl)phenyl)-2-(5H)-furanone;

3-(4-methylsulfonyl)phenyl-2-phenyl-5-trifluoromethylpyridine;

2-(3-chlorophenyl)-3-(4-methylsulfonyl)phenyl-5-trifluoromethyl-pyridine;

2-(4-chlorophenyl)-3-(4-methylsulfonyl)phenyl-5-trifluoromethyl-pyridine;

2-(4-fluorophenyl)-3-(4-methylsulfonyl)phenyl-5-trifluoromethyl-pyridine;

3-(4-methylsulfonyl)phenyl-2-(3-pyridinyl)-5-trifluoromethylpyridine;

5-methyl-3-(4-methylsulfonyl)phenyl-2-phenylpyridine;

2-(4-chlorophenyl)-5-methyl-3-(4-methylsulfonyl)phenylpyridine;

5-methyl-3-(4-methylsulfonyl)phenyl-2-(3-pyridinyl)pyridine;

5-chloro-2-(4-chlorophenyl)-3-(4-methylsulfonyl)phenylpyridine;

5-chloro-3-(4-methylsulfonyl)phenyl-2-(2-pyridinyl)pyridine;

5-chloro-3-(4-methylsulfonyl)phenyl-2-(3-pyridinyl)pyridine;

5-chloro-3-(4-methylsulfonyl)phenyl-2-(4-pyridinyl)pyridine;

5-chloro-3-(4-methylsulfonyl)phenyl-2-(2-methyl-5-pyridinyl)pyridine;

2-(4-chlorophenyl)-3-(4-methylsulfonyl)phenylpyridinyl-5-carboxylic acid methyl ester;

2-(4-chlorophenyl)-3-(4-methylsulfonyl)phenylpyridinyl-5-carboxylic acid;

5-cyano-2-(4-chlorophenyl)-3-(4-methylsulfonyl)phenylpyridine;

5-chloro-3-(4-methylsulfonyl)phenyl-2-(3-pyridyl)pyridine hydromethanesulfonate;

5-chloro-3-(4-methylsulfonyl)phenyl-2-(3-pyridyl)pyridine hydrochloride;

5-chloro-3-(4-methylsulfonyl)phenyl-2-(2-methyl-5-pyridinyl)pyridine hydrochloride;

5-chloro-3-(4-methylsulfonyl)phenyl-2-(2-ethyl-5-pyridinyl)pyridine;

5-chloro-3-(4-methylsulfonyl)phenyl-2-(2-ethyl-5-pyridinyl)pyridine hydromethanesulfonate;

3-(3,4-difluorophenoxy)-5,5-dimethyl-4-(4-(methylsulfonyl)phenyl)-5H-furan-2-one;

3-(3-fluorophenoxy)-5,5-dimethyl-4-(4-(methylsulfonyl)phenyl)-5H-furan-2-one;

3-(3,5-difluorophenoxy)-5,5-dimethyl-4-(methylsulfonyl)phenyl)-5H-furan-2-one;

3-phenoxy-5,5-dimethyl-4-(4-(methylsulfonyl)phenyl)-5H-furan-2-one;

3-(2,4-difluorophenoxy)-5,5-dimethyl-4-(4-(methylsulfonyl)phenyl)-5H-furan-2-one;

3-(4-chlorophenoxy)-5,5-dimethyl-4-(4-(methylsulfonyl)phenyl)-5H-furan-2-one;

3-(3,4-dichlorophenoxy)-5,5-dimethyl-4-(methylsulfonyl)phenyl)-5H-furan-2-one;

3-(4-fluorophenoxy)-5,5-dimethyl-4-(4-(methylsulfonyl)phenyl)-5H-furan-2-one;

3-(4-fluorophenylthio)-5,5-dimethyl-4-(4-(methylsulfonyl)phenyl)-5H-furan-2-one;

3-(3,5-difluorophenylthio)-5,5-dimethyl-4-(4-(methylsulfonyl)phenyl)-5H-furan-2-one;

3-phenylthio-5,5-dimethyl-4-(4-(methylsulfonyl)phenyl)-5H-furan-2-one;

3-(N-phenylamino)-5,5-dimethyl-4-(4-(methylsulfonyl)phenyl)-5H-furan-2-one;

3-(N-methyl-N-phenylamino)-5,5-dimethyl-4-(4-(methylsulfonyl)phenyl)-5H-furan-2-one;

3-cyclohexyloxy-5,5-dimethyl-4-(4-(methylsulfonyl)phenyl)-5H-furan-2-one;

3-phenylthio-4-(4-(methylsulfonyl)phenyl)-5H-furan-2-one;

3-benzyl-5,5-dimethyl-4-(4-(methylsulfonyl)phenyl)-5H-furan-2-one;

3-(3,4-difluorophenylhydroxymethyl)-5,5-dimethyl-4-(4-(methylsulfonyl)phenyl)-5H-furan-2-one;

3-(3,4-difluorobenzoyl)-5,5-dimethyl-4-(4-(methylsulfonyl)phenyl)-5H-furan-2-one;

3-benzoyl-5,5-dimethyl-4-(4-(methylsulfonyl)phenyl)-5H-furan-2-one;

4-(4-(methylsulfonyl)phenyl)-3-phenoxy-1-oxaspiro[4.4]non-3-en-2-one;

4-(4-(methylsulfonyl)phenyl)-3-phenylthio-1-oxaspiro[4.4]non-3-en-2-one;

4-(2-oxo-3-phenylthio-1-oxaspiro[4.4]non-3-en-4-yl)benzenesulfonamide;

3-(4-fluorobenzyl)-5,5-dimethyl-4-(4-(methylsulfonyl)phenyl)-5H-furan-2-one;

3-(3,4-difluorophenoxy)-5-methoxy-5-methyl-4-(4-(methylsulfonyl)phenyl)-5H-furan-2-one;

3-(5-chloro-2-pyridyloxy)-5,5-dimethyl-4-(4-(methylsulfonyl)phenyl)-5H-furan-2-one;

3-(2-pyridyloxy)-5,5-dimethyl-4-(4-(methylsulfonyl)phenyl)-5H-furan-2-one;

3-(6-methyl-2-pyridyloxy)-5,5-dimethyl-4-(4-(methylsulfonyl)phenyl)-5H-furan-2-one;

3-(3-isoquinolinoxy)-5,5-dimethyl-4-(4-(methylsulfonyl)phenyl)-5H-furan-2-one;

3-(4-(methylsulfonyl)phenyl)-2-phenoxycyclopent-2-enone;

3-(4-(methylsulfonyl)phenyl)-2-(3,4-difluorophenoxy)cyclopent-2-enone;

5,5-dimethyl-4-(4-methylsulfonylphenyl)-3-(5-bromopyridin-2-yloxy)-5H-furan-2-one;

5,5-dimethyl-4-(4-methylsulfonylphenyl)-3-(2-propoxy)-5H-furan-2-one;

2-(3,4-difluorophenoxy)-3-(4-methylsulfonylphenyl)-cyclopent-2-enone;

3-(5-benzothiophenyloxy)-5,5-dimethyl-4-(4-(methylsulfonyl)phenyl)-5H-furan-2-one;

5,5-dimethyl-4-(4-methylsulfonyl-phenyl)-3-(pyridyl-4-oxy)-5H-furan-2-one;

5,5-dimethyl-4-(4-methylsulfonyl-phenyl)-3-(pyridyl-3-oxy)-5H-furan-2-one;

3-(2-methyl-5-pyridyloxy)-5,5-dimethyl-4-(4-(methylsulfonyl)phenyl)-5H-furan-2-one;

3-(2-fluoro-4-trifluoromethyl)phenoxy-4-(4-methylsulfonyl)phenyl)-5,5-dimethyl-5H-furan-2-one;

3-(5-chloro-2-pyridylthio)-5,5-dimethyl-4-(4-methylsulfonyl)phenyl-5H-furan-2-one;

2-(3,5-difluorophenoxy)-3-(4-methylsulfonylphenyl)-cyclopent-2-enone;

3-(2-pyrimidinoxy)-5,5-dimethyl-4-(4-methylsulfonyl)phenyl-5H-furan-2-one;

3-(3-methyl-2-pyridyloxy)-5,5-dimethyl-4-(4-methylsulfonyl)phenyl-5H-furan-2-one;

3-(3-chloro-5-pyridyloxy)-5,5-dimethyl-4-(4-(methylsulfonyl)phenyl)-5H-furan-2-one;

3-(3-(1,2,5-thiadiazolyl)oxy)-4-(4-(methylsulfonyl)phenyl)-5,5-dimethyl-5H-furan-2-one;

3-(5-isoquinolinoxy)-5,5-dimethyl-4-(4-methylsulfonyl)phenyl-5H-furan-2-one;

3-(6-amino-2-pyridyloxy)-5,5-dimethyl-4-(4-(methylsulfonyl)phenyl)-5H-furan-2-one;

3-(3-chloro-4-fluoro)phenoxy-4-(methylsulfonyl)phenyl)-5,5-dimethyl-5H-furan-2-one;

3-(6-quinolinoxy)-5,5-dimethyl-4-(4-(methylsulfonyl)phenyl)-5H-furan-2-one;

3-(5-nitro-2-pyridyloxy)-5,5-dimethyl-4-(4-methylsulfonyl)phenyl-5H-furan-2-one;

3-(2-thiazolylthio)-5,5-dimethyl-4-(4-(methylsulfonyl)phenyl)-5H-furan-2-one;

3-(3-chloro-5-pyridyloxy)-5,5-dimethyl-4-(4-(methylsulfonyl)phenyl)-5H-furan-2-one;

5,5-dimethyl-4-(4-methylsulfonylphenyl)-3-(2-propoxy)-5H-furan-2-one;

3-(3-trifluoromethyl)phenoxy-4-(4-methylsulfonyl)phenyl)-5,5-dimethyl-5H-furan-2-one;

5,5-dimethyl-(4-(4-methylsulfonyl)phenyl)-3-(piperidine-1-carbonyl)-5-H-furan-2-one;

5,5-dimethyl-3-(2-Butoxy)-4-(4-methylsulfonylphenyl)-5H-furan-2-one;

5,5-dimethyl-4-(4-methylsulfonylphenyl)-3-(3-pentoxy)-5H-furan-2-one;

2-(5-chloro-2-pyridyloxy)-3-(4-methylsulfonyl)phenylcyclopent-2-enone;

3-(4-methyl-2-pyridyloxy)-5,5-dimethyl-4-(4-methylsulfonyl)phenyl-5H-furan-2-one;

(5R)-3-(3,4-difluorophenoxy)-5-ethyl-5-methyl-4-(4-methylsulfonyl)phenyl-5H-furan-2-one;

(5R)-3-(4-chlorophenoxy)-5-ethyl-5-methyl-4-(4-methylsulfonyl)phenyl-5H-furan-2-one;

3-(2-methyl-3-pyridyloxy)-5,5-dimethyl-4-(4-methylsulfonyl)phenyl-5H-furan-2-one;

3-(4-methyl-5-nitro-2-pyridyloxy)-5,5-dimethyl-4-(4-methylsulfonyl)phenyl-5H-furan-2-one;

3-(5-chloro-4-methyl-2-pyridyloxy)-5,5-dimethyl-4-(4-methylsulfonyl)phenyl-5H-furan-2-one;

3-(5-fluoro-4-methyl-2-pyridyloxy)-5,5-dimethyl-4-(4-methylsulfonyl)phenyl-5H-furan-2-one;

3-(3-chloro-2-pyridyloxy)-5,5-dimethyl-4-(4-methylsulfonyl)phenyl-5H-furan-2-one;

3-(4-fluorophenoxy)-5-methyl-4-(4-methylsulfonyl)phenyl-5-propyl-5H-furan-2-one;

3-(N,N-diethylamino)-5,5-dimethyl-4-(4-(methylsulfonyl)phenyl)-5H-furan-2-one;

5,5-dimethyl-4-(4-methylsulfonyl-phenyl)-3-(3,5-dichloro-2-pyridyloxy)-5H-furan-2-one;

(5R)-3-(4-bromophenoxy)-5-ethyl-5-methyl-4-(4-methylsulfonyl)phenyl-5H-furan-2-one;

(5R)-3-(4-methoxyphenoxy)-5-ethyl-5-methyl-4-(4-methylsulfonyl)phenyl-5H-furan-2-one;

(5R)-3-(5-chloro-2-pyridyloxy)-5-methyl-4-(4-methylsulfonyl)phenyl-5-(2,2,2-trifluoroethyl)-5H-furan-2-one;

3-(5-chloro-2-pyridyloxy)-5-methyl-4-(4-methylsulfonyl)phenyl-5-propyl-5H-furan-2-one 3-(1-cyclopropyl-ethoxy)-5,5-dimethyl-4-(4-methyl sulfonyl)phenyl)-5H-furan-2-one;

5-methyl-4-(4-(methylsulfonyl)phenyl)-3-(2-(propoxy)-5-(2-trifluoroethyl)-5H-furan-2-one;

5(R)-5-ethyl-5-methyl-4-(4-(methylsulfonyl)phenyl)-3-(2-propoxy)-5H-furan-2-one;

5,5-dimethyl-3-(2,2-dimethylpropyloxy)-4-(4-(methylsulfonyl)phenyl)-5H-furan-2-one;

5(R)-3-(1-cyclopropyl-ethoxy)-5-ethyl-5-methyl-4-(4-(methyl sulfonyl)phenyl-5H-furan-2-one;

5(S)-5-ethyl-5-methyl-4-(4-(methylsulfonyl)phenyl)-3-(2-propoxy)-5H-furan-2-one;

3-(1-cyclopropylethoxy)-5,5-dimethyl-4-(4-(methylsulfonyl)phenyl)-5H-furan-2-one;

3-(1-cyclopropylethoxy)-5,5-dimethyl-4-(4-(methylsulfonyl)phenyl)-5H-furan-2-one;

5,5-dimethyl-3-(isobutoxy)-4-(4-(methylsulfonyl)phenyl)-5H-furan-2-one;

3-(4-bromophenoxy)-5,5-dimethyl-4-(4-(methylsulfonyl)phenyl)-5H-furan-2-one;

3-(2-quinolinoxy)-5,5-dimethyl-4-(4-(methylsulfonyl)phenyl)-5H-furan-2-one;

3-(2-chloro-5-pyridyloxy)-5,5-dimethyl-4-(4-(methylsulfonyl)phenyl)-5H-furan-2-one;

3-(6-benzothiazolyloxy)-5,5-dimethyl-4-(4-(methylsulfonyl)phenyl)-5H-furan-2-one;

3-(6-chloro-2-pyridyloxy)-5,5-dimethyl-4-(4-(methylsulfonyl)phenyl)-5H-furan-2-one;

3-(4-quinazolyloxy)-5,5-dimethyl-4-(4-(methylsulfonyl)phenyl)-5H-furan-2-one;

(5R)-3-(5-fluoro-2-pyridyloxy)-5-ethyl-5-methyl-4-(4-methylsulfonyl)phenyl-5H-furan-2-one;

(5R)-3-(4-fluorophenoxy)-5-ethyl-5-methyl-4-(4-methylsulfonyl)phenyl-5H-furan-2-one;

(5R)-3-(5-fluoro-2-pyridyloxy)-5-methyl-4-(4-methylsulfonyl)phenyl-5-(2,2,2-trifluoroethyl)-5H-furan-2-one;

3-(1-isoquinolinyloxy)-5,5-dimethyl-4-(methylsulfonyl)phenyl-5H-furan-2-one;

(5R)-3-(4-fluorophenoxy)-5-methyl-4-(4-methylsulfonyl)phenyl-5-(2,2,2-trifluoroethyl)-5H-furan-2-one;

3-(3-fluoro-2-pyridyloxy)-5,5-dimethyl-4-(4-methylsulfonyl)phenyl-5H-furan-2-one;

(5R)-3-(3,4-difluorophenoxy)-5-methyl-4-(4-methylsulfonyl)phenyl-5-(2,2,2-trifluoroethyl)-5H-furan-2-one;

(5R)-3-(5-chloro-2-pyridyloxy)-5-ethyl-5-methyl-4-(4-methylsulfonyl)phenyl-5H-furan-2-one;

3-(3,4-difluorophenoxy)-5-methyl-5-trifluoromethyl-4-(4-methylsulfonyl)phenyl-5H-furan-2-one;

3-(3,4-difluorophenoxy)-5-methyl-4-(4-(methylsulfonyl)phenyl)-5-propyl-5H-furan-2-one;

3-cyclobutyloxy-5,5-dimethyl-4-(4-methylsulfonylphenyl-5H-furan-2-one;

3-(1-indanyloxy)-5,5-dimethyl-4-(4-(methylsulfonyl)phenyl)-5H-furan-2-one;

3-(2-indanyloxy)-5,5-dimethyl-4-(4-methylsulfonyl)phenyl)-5H-furan-2-one;

3-cyclopentyloxy-5,5-dimethyl-4-(4-methylsulfonylphenyl)-5H-furan-2-one;

3-(3,3-dimethylcyclopentyloxy)-5,5-dimethyl-4-(4-methylsulfonyl-phenyl)-5H-furan-2-one;

3-isopropoxy-5-methyl-4-(4-methylsulfonylphenyl)-5-propyl-5H-furan-2-one;

3-(2-methoxy-5-pyridyloxy)-5,5-dimethyl-4-(4-methylsulfonyl)phenyl-5H-furan-2-one;

3-(5-methyl-2-pyridyloxy)-5,5-dimethyl-4-(4-methylsulfonyl)phenyl-5H-furan-2-one;

(5RS)-3-(3,4-difluorophenoxy)-5-methyl-4-(4-methylsulfonyl)phenyl-5-(2,2,2-trifluoroethyl)-5H-furan-2-one;

3-(3-chloro-4-methoxyphenoxy)-5,5-dimethyl-4-(4-methylsulfonyl)phenyl-5H-furan-2-one;

(5R)-3-(3-chloro-4-methoxyphenoxy)-5-ethyl-5-methyl-4-(4-methylsulfonyl)phenyl-5H-furan-2-one;

(5R)-3-(4-chlorophenoxy)-5-trifluoroethyl-5-methyl-4-(4-methylsulfonyl)phenyl-5H-furan-2-one, (5R)-3-(4-bromophenoxy)-5-trifluoroethyl-5-methyl-4-(4-methylsulfonyl)phenyl-5H-furan-2-one;

5-cyclopropylmethyl-3-(3,4-difluorophenoxy)-5-methyl-(4-methylsulfonyl)phenyl-5H-furan-2-one;

(5R)-3-(3-fluorophenoxy)-5-ethyl-5-methyl-4-(4-methylsulfonyl)phenyl-5H-furan-2-one;

(5R)-3-(4-chloro-3-fluorophenoxy)-5-ethyl-5-methyl-4-(4-methylsulfonyl)phenyl-5H-furan-2-one;

(5R)-3-phenoxy-5-ethyl-5-methyl-4-(4-methylsulfonyl)phenyl-5H-furan-2-one;

(5R)-3-(4-chloro-3-methylphenoxy)-5-ethyl-5-methyl-4-(4-methylsulfonyl)phenyl-5H-furan-2-one;

3-(4-chloro-3-methylphenoxy)-5-5-dimethyl-4-(4-methylsulfonyl)phenyl-5H-furan-2-one;

(5R)-3-(5-bromo-2-pyridyloxy)-4-(4-methylsulfonylphenyl)-5-methyl-5-(2,2,2-trifluoroethyl)-5H-furan-2-one;

(5R)-3-(5-bromo-2-pyridyloxy)-4-(4-methylsulfonylphenyl)-5-ethyl-5-methyl-5H-furan-2-one;

3-(5-chloro-6-methyl-2-pyridyloxy)-5,5-dimethyl-4-(4-methylsulfonyl)phenyl-5H-furan-2-one;

3-(5-cyclopropyl-2-pyridyloxy)-5,5-dimethyl-4-(4-methylsulfonyl)phenyl-5H-furan-2-one;

3-(1-cyclopropylethoxy)-4-(4-methylsulfonyl)phenyl-5H-furan-2-one; and 3-(cyclopropylmethoxy)-4-(4-methylsulfonyl)phenyl-5H-furan-2-one;

or a pharmaceutically acceptable salt or stereoisomer thereof.

Inhibitors of COX-2 that are particularly useful in the instant method of treatment are:

3-phenyl-4-(4-(methylsulfonyl)phenyl)-2-(5H)-furanone; and

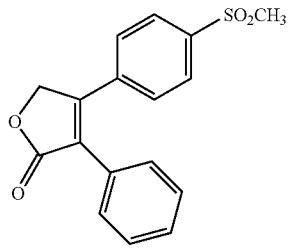

5-chloro-3-(4-methylsulfonyl)phenyl-2-(2-methyl-5-pyridinyl)pyridine;

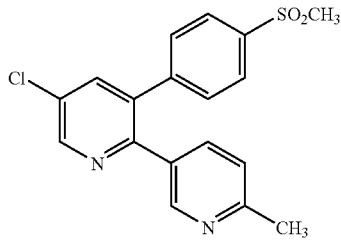

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

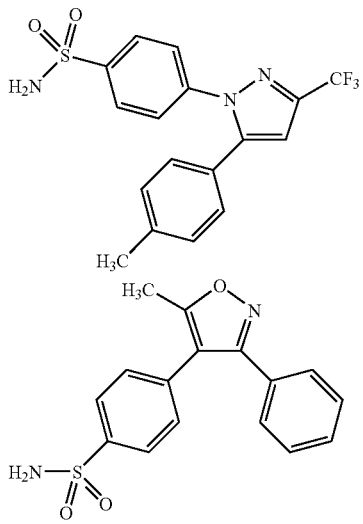

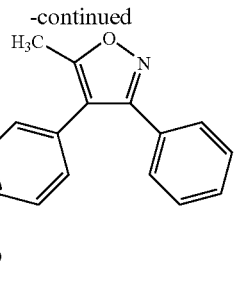

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl) phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium. (Amirkhosravi, *Platelets* 10, 285-292, 1999). Therefore, the present compounds can serve to inhibit metastasis, alone or in combination with GP IIb/IIIa antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The scope of the invention therefore encompasses the use of the instantly claimed compounds in combination with a second compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors to be used as the second compound are a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamido-triazole, combretastatin A-4, squalamine, 6-O-chloroacetyl-carbonyl)-fumagillol, thalidomide, angiostatin, troponin-1, or an antibody to VEGF. Preferred estrogen receptor modulators are tamoxifen and raloxifene.

Also included in the scope of the claims is a method of treating cancer which comprises administering a therapeutically effective amount of a compound of Formula I in combination with radiation therapy and/or in combination with a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formula I in combination with paclitaxel or trastuzumab.

The invention further encompasses a method of treating or preventing cancer which comprises administering a therapeutically effective amount of a compound of Formula I in combination with a COX-2 inhibitor.

These and other aspects of the invention will be apparent from the teachings contained herein.

Definitions

The compounds of the present invention may have asymmetric centers, chiral axes, and chiral planes (as described in: E. L. Eliel and S. H. Wilen, *Stereo-chemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms, and mixtures thereof, are intended to be encompassed by the scope of the invention, even though only one tautomeric structure is depicted.

When any variable occurs more than one time in any constituent, such as $R^4$ or n, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and unbranched, cyclic and acyclic saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement and may be cyclic or acyclic. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, cyclopropyl, methyl-cyclopropyl, 2,2-dimethyl-cyclobutyl, 2-ethylcyclopentyl, cyclohexyl, and so on. In some instances, definitions may appear for the same variable reciting both alkyl and cycloalkyl when a different number of carbons is intended for the respective substituents. The use of both terms in one definition should not be interpreted to mean in another definition that "alkyl" does not encompass "cycloalkyl" when only "alkyl" is used. "Cycloalkyl", however, does not encompass non-cyclic alkyls.

"Alkoxy" represents an alkyl group of indicated number of carbon atoms as defined above attached through an oxygen bridge. The term "$C_{1-6}$ alkoxy" is therefore equivalent to "$OC_{1-6}$ alkyl".

As used herein, "aryl" is intended to mean phenyl and substituted phenyl, including moieties with a fused benzo group. Examples of such aryl elements include phenyl, naphthyl, tetrahydronaphthyl, indanyl, biphenyl, phenanthryl, anthryl or acenaphthyl. In cases where the aryl substituent is bicyclic, as in tetrahydronaphthyl, it is understood that attachment is via the phenyl ring. Unless otherwise indicated, "aryl" includes phenyls substituted with one or more substituents.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro, fluoro, bromo and iodo.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The alkyl, cycloalkyl, aryl, heteroaryl and heterocyclyl substituents may be substituted or unsubstituted, unless specifically defined otherwise. For example, a ($C_1$-$C_6$)alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —(C=O)CH$_2$CH(OH)CH$_3$, —(C=O)OH, —CH$_2$(OH)CH$_2$CH(O), and so on.

The pharmaceutically acceptable salts encompassed by the present invention can be synthesized from the disclosed compounds which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Similarly, the salts of the acidic compounds are formed by reactions with conventional inorganic or organic bases.

In certain instances, $R^5$ and $R^6$ are defined such that they can be taken with the nitrogen to which they are attached to form a monocyclic or bicyclic heterocycle with 5-7 members in each ring, said heterocycle optionally substituted with one or more substituents selected from halo, $C_{1-6}$ alkyl, $C_{1-6}$ alkyloxy, $OCF_3$, $CO_2R^d$, $(C=O)R^d$, aryl, heterocyclyl, $SO_2R^d$ and OH. Examples of the heterocycles that can thus be formed include, but are not limited to the following, keeping in mind that the heterocycle is optionally substituted as defined above.

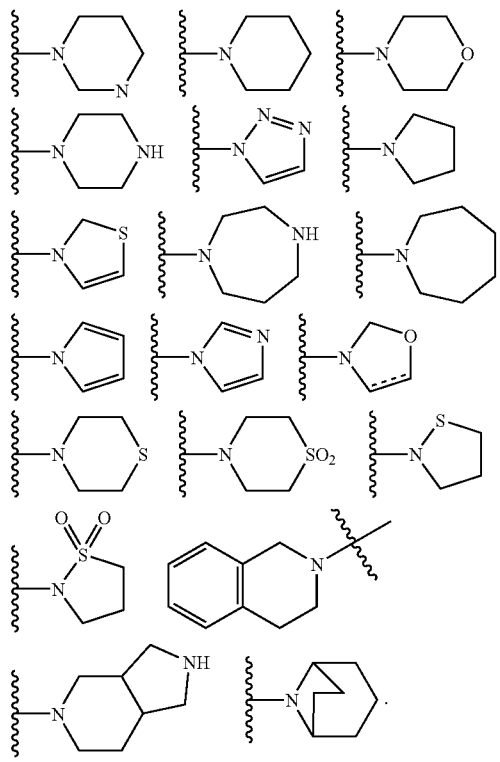

Preferably $R^1$ is H.

Preferably $R^2$ is CN, substituted or unsubstituted phenyl, $(C=O)NR^aR^b$, or halo. Most preferably $R^2$ is CN, substituted or unsubstituted phenyl, or $(C=O)NR^aR^b$.

$R^3$ is preferably H. When a substituent is defined as "heterocyclyl" or "heterocycle", preferred heterocycles are 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes. Substituent numbering as shown in the schemes does not necessarily correlate to that used in the claims.

Schemes

As shown in Scheme A, the compounds of the instant invention may be synthesized by activating the amino thiazole A-1 with p-nitrophenylchloroformate A-2, followed by coupling with the appropriate secondary amine A-4. Scheme B illustrates one possible approach to the synthesis of compounds wherein the phenyl of the thiazole is substituted. By starting with the substituted benzyl alcohol B-1, it is possible to to form the activated amino thiazole B-8, which can then be substituted for A-3 in Scheme A and coupled with a secondary amine to yield a compound of the instant invention.

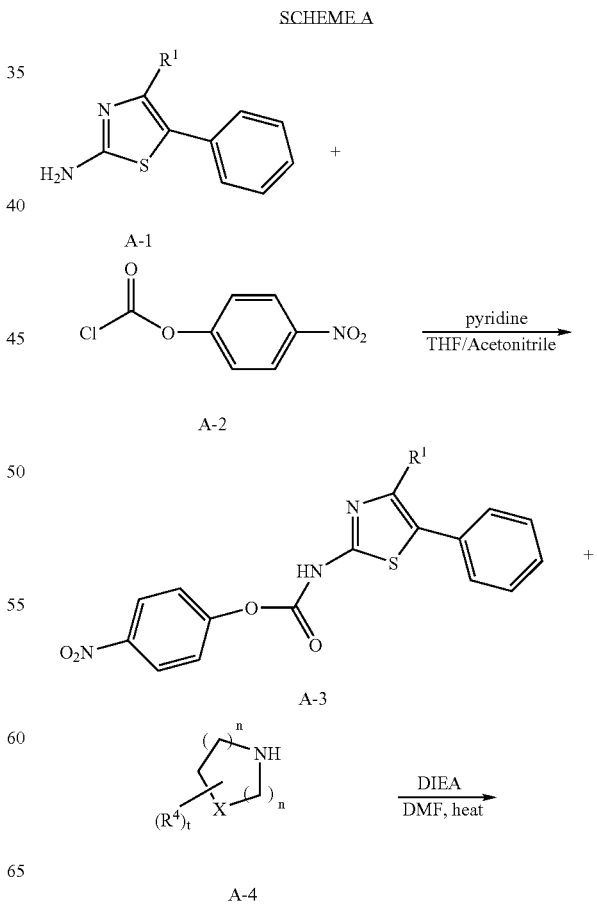

SCHEME A

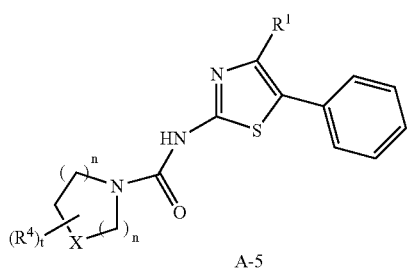

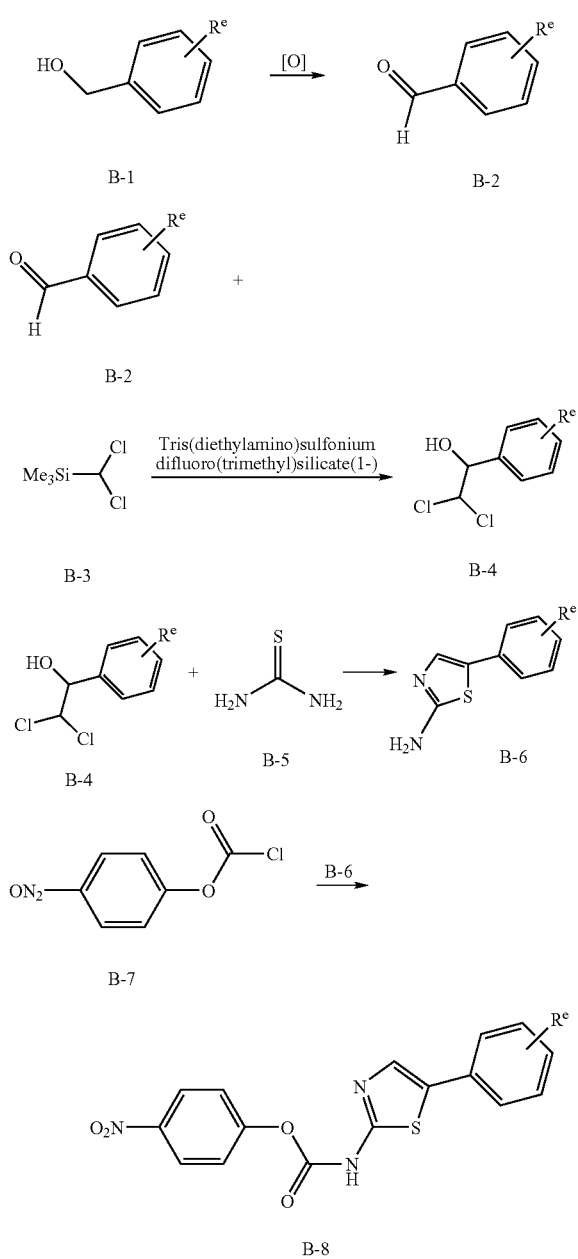

Assays

The compounds of the instant invention described in the Examples were tested by the assays described below and were found to have kinase inhibitory activity. Other assays are known in the literature and could be readily performed by those of skill in the art (see, for example, Dhanabal et al., Cancer Res. 59:189-197; Xin et al., J. Biol. Chem. 274: 9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549).

I. VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677-1683.) and Flt-1 (Shibuya, M. et al. Oncogene (1990) vol. 5, pp. 519-524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in *Spodoptera frugiperda* (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 μg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 μg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 μg/mL of each leupeptin, pepstatin and aprotinin and 1 mM phenylmethylsuflonyl fluoride.

10× reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10× substrate: 750 μg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,00×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 μl of inhibitor or control to the assay in 50% DMSO.
2. Add 35 μl of reaction mix containing 5 μl of 10× reaction buffer, 5 μl 25 mM ATP/10 μCi [$^{33}$P]ATP (Amersham), and 5 μl 10× substrate.
3. Start the reaction by the addition of 10 μl of KDR (25 nM) in enzyme dilution buffer.
4. Mix and incubate at room temperature for 15 minutes.
5. Stop by the addition of 50 μl stop solution.
6. Incubate for 15 minutes at 4° C.
7. Transfer a $^{90}$ μl aliquot to filter plate.
8. Aspirate and wash 3 times with wash solution.
9. Add 30 μl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs: HUVECs frozen as primary culture isolates are obtained from Clonetics Corp. Cells are maintained in Endothelial Growth Medium (EGM; Clonetics) and are used for mitogenic assays described in passages 3-7 below.
Culture plates: NUNCLON 96-well polystyrene tissue culture plates (NUNC #167008).
Assay medium: Dulbecco's modification of Eagle's medium containing 1 g/mL glucose (low-glucose DMEM; Mediatech) plus 10% (v/v) fetal bovine serum (Clonetics).
Test compounds: Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.
10× Growth factors: Solutions of human $VEGF_{165}$ (500 ng/mL; R&D Systems) and bFGF (10 ng/mL; R&D Systems) are prepared in Assay Medium.
10× [$^3$H]Thymidine: [Methyl-$^3$H]thymidine (20 Ci/mmol; Dupont-NEN) is diluted to 80 μCi/mL in low-glucose DMEM.
Cell wash medium: Hank's balanced salt solution (Mediatech) containing 1 mg/mL bovine serum albumin (Boehringer-Mannheim).
Cell lysis solution: 1 N NaOH, 2% (w/v) $Na_2CO_3$.

Method

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% $CO_2$.
2. Growth-arrest medium is replaced by 100 μL Assay Medium containing either vehicle (0.25% [v/v] DMSO) or the desired final concentration of test compound. All determinations are performed in triplicate. Cells are then incubated at 37° C. with 5% $CO_2$ for 2 hours to allow test compounds to enter cells.
3. After the 2-hour pretreatment period, cells are stimulated by addition of 10 μL/well of either Assay Medium, 10× VEGF solution or 10× bFGF solution. Cells are then incubated at 37° C. and 5% $CO_2$.
4. After 24 hours in the presence of growth factors, 10×[$^3$H]thymidine (10 μL/well) is added.
5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the compounds of Formula I are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with $IC_{50}$ values between 0.01-5.0 μM. These compounds may also show selectivity over related tyrosine kinases (e.g., FGFR1 and the Src family; for relationship between Src kinases and VEGFR kinases, see Eliceiri et al., Molecular Cell, Vol. 4, pp. 915-924, December 1999).

III. FLT-1 Kinase Assay

Flt-1 was expressed as a GST fusion to the Flt-1 kinase domain and was expressed in baculovirus/insect cells. The following protocol was employed to assay compounds for Flt-1 kinase inhibitory activity:

1. Inhibitors were diluted to account for the final dilution in the assay, 1:20.
2. The appropriate amount of reaction mix was prepared at room temperature:
   10× Buffer (20 mM Tris pH 7.4/0.1 M NaCl/1 mM DTT final)
   0.1M $MnCl_2$ (5 mM final)
   pEY substrate (75 μg/mL)
   ATP/[$^{33}$P]ATP (2.5 μM/1 μCi final)
   BSA (500 μg/mL final).
3. 5 μL of the diluted inhibitor was added to the reaction mix. (Final volume of 5 μL in 50% DMSO). To the positive control wells, blank DMSO (50%) was added.
4. 35 μL of the reaction mix was added to each well of a 96 well plate.
5. Enzyme was diluted into enzyme dilution buffer (kept at 4° C.).
6. 10 μL of the diluted enzyme was added to each well and mix (5 nM final). To the negative control wells, 10 μL 0.5 M EDTA was added per well instead (final 100 mM).

7. Incubation was then carried out at room temperature for 30 minutes.
8. Stopped by the addition of an equal volume (50 µL) of 30% TCA/0.1M Na pyrophosphate.
9. Incubation was then carried out for 15 minutes to allow precipitation.
10. Transferred to Millipore filter plate.
11. Washed 3× with 15% TCA/0.1M Na pyrophosphate (125 µL per wash).
12. Allowed to dry under vacuum for 2-3 minutes.
13. Dryed in hood for ~20 minutes.
14. Assembled Wallac Millipore adapter and added 50 µL of scintillant to each well and counted.

EXAMPLES

Examples provided are intended to assist in a further understanding of the invention. Particular materials employed, species and conditions are intended to be illustrative of the invention and not limiting of the reasonable scope thereof.

Example 1

Scheme 1: Synthesis of 2-(4-nitrophenoxycarbonyl)amino-5-phenylthiazole 1-3

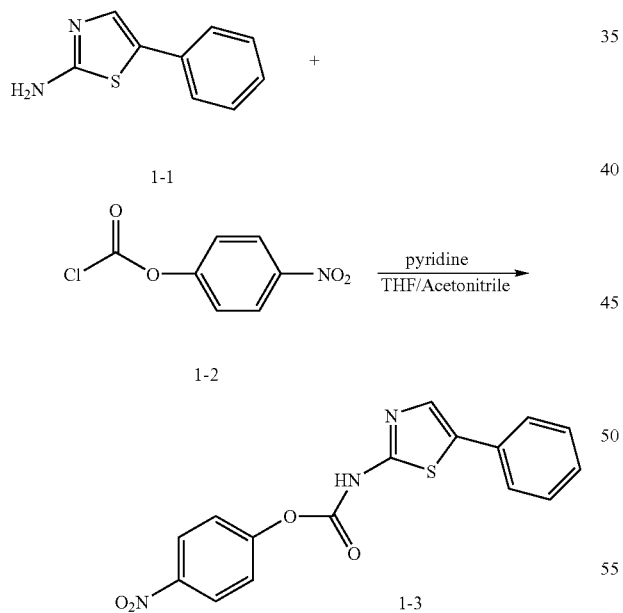

To a solution of 1.36 g (7.72 mmol) of 2-aminothiazole 1-1 in 24 mL of 7:1 THF/acetonitrile was added 1.56 g (7.72 mmol) of p-nitrophenylchloroformate, 1-2, followed by 781 µl (9.65 mmol) of pyridine. A thick yellow precipitate formed immediately. The resulting suspension was stirred vigorously at room temperature for 18 hours and then filtered. The yellow solid precipitate was washed several times with THF and dried in vacuo to provide 1-3.

Example 2

Scheme 2: Synthesis of N-(5-phenylthiazol-2-yl)-N'-[4-(2-pyridyl)piperazin-1-yl]urea (2-3)

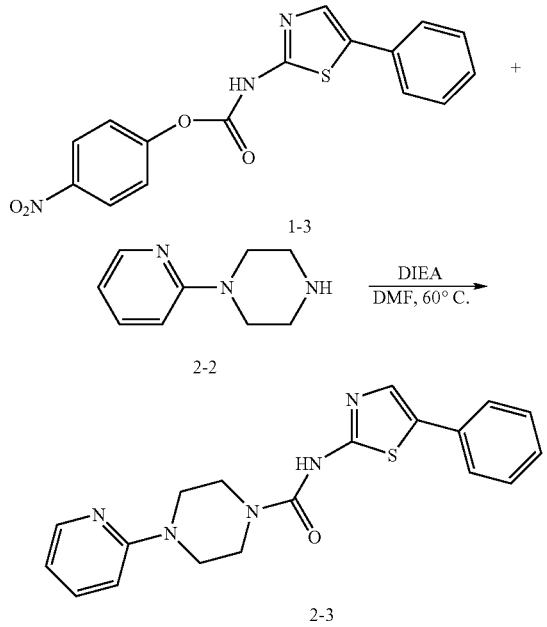

A solution of 100 mg (0.29 mmol) of 2-(4-nitrophenoxycarbonyl) amino-5-phenylthiazole 1-3, 44 µl (0.29 mmol) of 4-(2-pyridyl)piperazine 2-2, and 54 µl (0.31 mmol) of diisopropylethylamine, DIEA, in 1 mL anhydrous dimethylformamide, DMF, was stirred at 60° C. under a nitrogen atmosphere for 1 hour. The reaction was then concentrated in vacuo to an orange-yellow oil. The oil was dissolved in chloroform and washed 5× with concentrated aqueous $NH_4OH$. The organic layer was dried over anhydrous $Na_2SO_4$, filtered, and concentrated in vacuo to an orange oil. The crude oil was purified by reversed phase preparatory LC, and the pure fractions concentrated and lyophilized to give the TFA salt of 2-3 as an amorphous white powder. $H^1$ NMR (DMSO-$d_6$): 3.62 (m, 4H), 3.69 (m, 4H), 6.81 (br t, 1H), 7.14 (br s, 1H), 7.28 (t, 1H), 7.41 (t, 2H), 7.57(d, 2H), 7.78 (m, 2H), 8.11 (dd, 1H). High Res. FAB MS: Theo. Mass=366.1383; measured mass=366.1399.

Example 3

N-(5-phenylthiazol-2-yl)-N'-[4-(2-pyrimidinyl)piperazin-1-yl]urea (3)

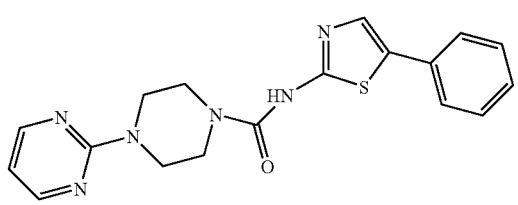

In a manner identical to that described above in Scheme 2, from 100 mg (0.29 mmol) of 2-(4-nitrophenoxycarbonyl)amino-5-phenylthiazole and 48 mg (0.29 mmol) of 4-(2-pyrimidinyl)piperazine was obtained the bis TFA salt of 3 as a fluffy white amorphous solid after lyophilization. H$^1$ NMR (DMSO-d$_6$): 3.61 (m, 4H), 3.72 (m, 4H), 6.70 (m, 1H), 7.45 (complex, 6H), 7.80 (s, 1H), 8.20 (m, 2H). High Res. FAB MS: Theo. Mass=367.1336; measured mass=267.1337.

Example 4

N-(5-phenylthiazol-2-yl)-N'-(4-aminopiperidin-1-yl)urea (4)

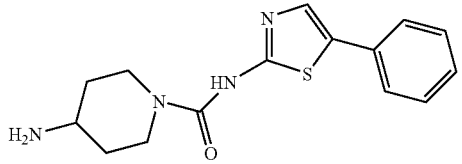

4

In a manner identical to that described above in Scheme 2, from 150 mg (0.44 mmol) of 2-(4-nitrophenoxycarbonyl)amino-5-phenylthiazole and 88 mg (0.44 mmol) of 4-Boc-amino-piperidine was obtained the crude Boc protected product. The product was dissolved in 1 mL TFA/1 mL methylene chloride and stirred at room temperature for 2 hours. The reaction was then concentrated in vacuo to give the crude product as a brown oil. The oil was purified by reversed phase preparatory LC to give the TFA salt of 4 as a fluffy white amorphous solid. H$^1$ NMR (DMSO-d6): 1.41 (dq, 2H), 1.91 (dd, 2H), 2.91 (t, 2H), 3.24 (m, 1H), 4.23 (dd, 2H), 7.28 (t, 1H), 7.40 (t, 2H), 7.56 (d, 2H), 7.77 (s, 1H), 7.88 (br s, 2H). High Res. FAB MS: Theo. Mass=303.1274; measured mass=303.1295.

Example 5

N-(5-phenylthiazol-2-yl)-N'-(piperazin-1-yl)urea (5)

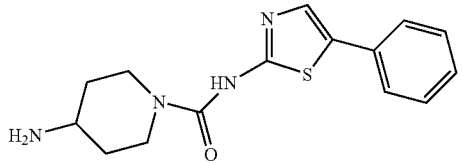

5

In a manner identical to that described above in Scheme 2, from 200 mg (0.59 mmol) of 2-(4-nitrophenoxycarbonyl)amino-5-phenylthiazole and 110 mg (0.59 mmol) of 1-Boc-piperazine was obtained the crude Boc protected product. The product was dissolved in 1 mL TFA/1 mL methylene chloride and stirred at room temperature for 2 hours. The reaction was concentrated in vacuo to give the crude product as a brown oil. The oil was purified by reversed phase preparatory LC to give the TFA salt of 5 as a fluffy white amorphous solid. H$^1$ NMR (DMSO-d6): 3.14 (br m, 4H), 3.74 (br m, 4H), 7.28 (t, 1H), 7.40 (t, 2H), 7.57 (d, 2H), 7.78 (s, 1H), 8.81 (br, s, 1H). High Res. FAB MS: Theo. Mass=289.1117; measured mass=289.1137.

SCHEME 6 N-(5-phenylthiazol-2-y-N'-[4-(2-pyrimidinoxy)piperidin-1-yl)]urea (6-4)

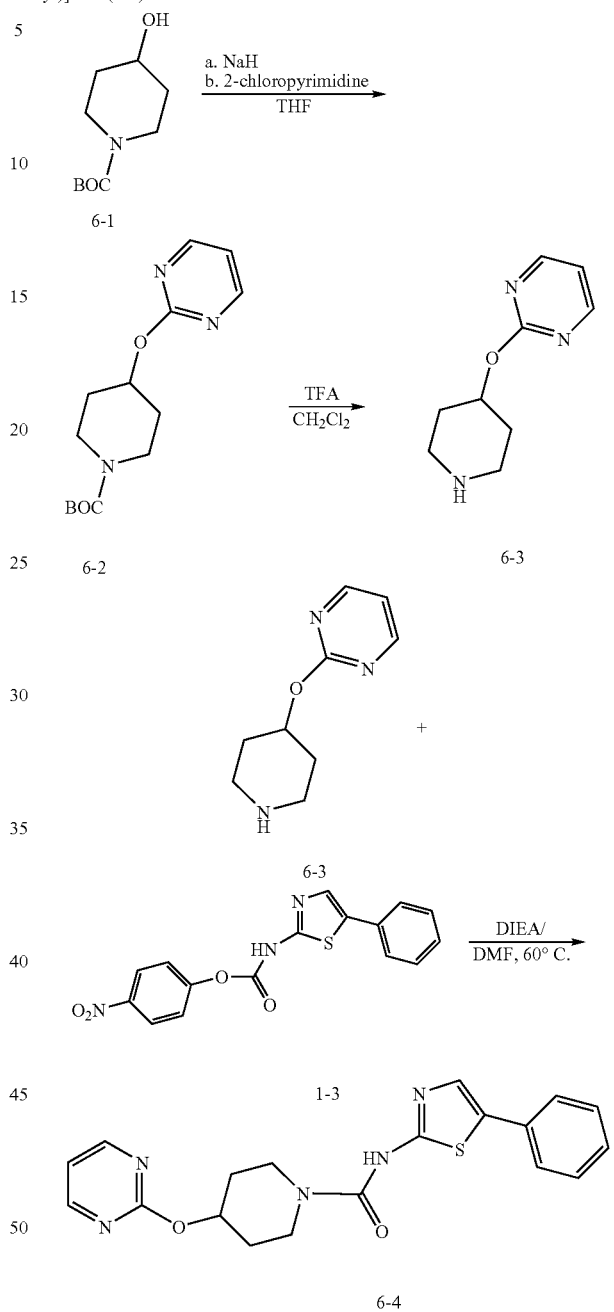

4-pyrimidinoxy-piperidine (6-3)

A solution of 405 mg (2.01 mmol) of N-Boc-4-hydroxypiperidine 6-1 in 2 mL anhydrous DMF was treated with 82 mg (2.02 mmol) of 60% NaH dispersion. After 30 minutes, the reaction was treated with 207 mg (1.81 mmol) of 2-chloro-pyrimidine which was added in one portion. The reaction was heated to 50° C. for 2 hours and then diluted with 3× its volume of water. The mixture was extracted twice with ethyl acetate. The combined extracts were dried over anhydrous MgSO$_4$, filtered, and concentrated in vacuo. The crude oil was purified by column chromatography over silica gel with 5% ethyl acetate in chloroform to afford 6-2. The purified material was dissolved in 1 mL methylene chloride/1 mL TFA and stirred at room temperature for 18 hours. The reaction was concentrated in vacuo to give the TFA salt of 4-pyrimidinoxy-piperidine 6-3 as an oil.

N-(5-phenylthiazol-2-yl)-N'-[4-(2-pyrimidinoxy) piperidin-1-yl)]urea (6-4)

In a manner identical to that described above in Scheme 2, 147 mg (0.43 mmol) of 2-(4-nitrophenoxycarbonyl) amino-5-phenylthiazole 1-3, 175 mg (0.43 mmol) of the TFA salt of 6-3 generated above, and 300 μl (1.72 mmol) of DIEA were used to afford the TFA salt of 6-4 as a fluffy white amorphous powder after lyophilization. H$^1$ NMR (DMSO-d6): 1.67 (m, 2H), 2.03 (m, 2H), 3.39 (dt, 2H), 3.44 (m, 2H), 5.20 (m, 1H), 7.14 (t, 1H), 7.27 (t, 1H), 7.40 (t, 2H), 7.57 (d, 2H), 7.76 (s, 1H), 8.61 (d, 2H). High Res. FAB MS: Theo. Mass=382.1332; measured mass=382.1362.

Example 7

N-(5-phenylthiazol-2-yl)-N'-(4-carboxypiperidin-1-yl)urea (7)

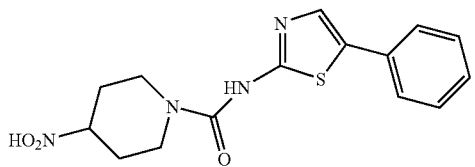

7

In a manner identical to that described above in Scheme 2, from 117 mg (0.34 mmol) of 2-(4-nitrophenoxycarbonyl) amino-5-phenylthiazole and 53 μl (0.34 mmol) of 4-carboethoxy-piperidine was obtained 90 mg of the crude ester product. The product was dissolved in 2 mL of 1 M LiOH/2 mL DME and stirred at room temperature for 18 hours. The reaction was then concentrated to remove the DME and acidified with 1N aq. KHSO$_4$. The mixture was extracted twice with ethyl acetate. The combined extracts were dried, filtered, and concentrated in vacuo to give a solid. The crude solid was purified by reversed phase prep LC to afford 7 as a fluffy white amorphous powder after lyophilization. H$^1$ NMR (DMSO-d6): 1.48 (m, 2H), 1.86 (m, 2H), 2.97 (dt, 2H), 3.60 (m, 1H), 4.09 (m, 2H), 7.26 (t, 1H), 7.39 (t, 2H), 7.55 (d, 2H), 7.75 (s, 1H). FAB MS: M+=331.

Example 8

N-(5-phenylthiazol-2-yl)-N'-(2,2,6,6-tetramethyl-4-aminopiperidin-4-yl) urea (8)

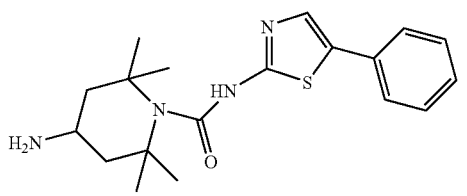

8

In a manner identical to that described above in Scheme 2, from 250 mg (0.73 mmol) of 2-(4-nitrophenoxycarbonyl) amino-5-phenylthiazole and 114 mg (0.73 mmol) of 2,2,6,6-tetramethyl-4-aminopiperidine was obtained 120 mg of the TFA salt of 8 as an amorphous white powder after lyophilization. H$^1$ NMR (DMSO-d6): 1.37 (s, 6H), 1.46 (s, 6H), 1.48 (m, 2M), 2.02 (dd, 2H), 4.07 (br m, 1H), 6.89 (d, 1H), 7.28 (t, 1H), 7.40 (t, 2H), 7.55 (d, 2H), 7.73 (s, 1H), 7.78 (br m, 1H), 8.65 (br m, 1H). High Res. FAB MS: Theo. Mass=359.1900; measured mass=359.1897.

Example 9

N-(5-phenylthiazol-2-yl)-N'-(3-(S)-aminopyrrolidin-1-yl)urea (9)

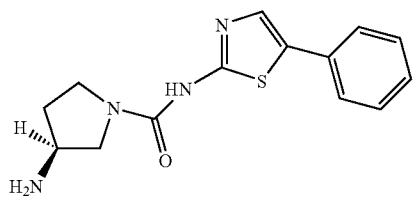

9

In a manner identical to that described above in Scheme 2, from 400 mg (1.17 mmol) of 2-(4-nitrophenoxycarbonyl) amino-5-phenylthiazole and 256 mg (1.17 mmol) of 3-(S)-trifluoroacetamido-pyrrolidine was obtained the crude trifluoroacetylated product. The product was dissolved in 3 mL methanol/1 mL DME/3 mL saturated. aqueous K$_2$CO$_3$ and stirred at 50° C. for 3 hours. The reaction was cooled, acidified to pH 7 with 1N KHSO$_4$, diluted with ethyl acetate and stirred. The mixture was then filtered and the layers separated. The aqueous layer was re-extracted with ethyl acetate. The combined ethyl acetate extracts were dried and concentrated in vacuo to give a yellow oil. The oil was purified by reversed phase preparatory LC to yield the TFA salt of 9 a fluffy white amorphous solid. H$^1$ NMR (DMSO-d6): 2.00 (br m, 1H), 2.24 (br m, 1H), 3.58 (m, 3H), 3.66 (br m, 1H), 3.88 (br m, 1H), 7.28 (t, 1H), 7.40 (t, 2H), 7.57 (d, 2H), 7.78 (s, 1H), 8.05 (br d, 2H). High Res. FAB MS: Theo. Mass=289.1118; measured mass=289.1125.

Example 10

N-(5-phenylthiazol-2-yl)-N'-(3-(R)-aminopyrrolidin-1-yl)urea (10)

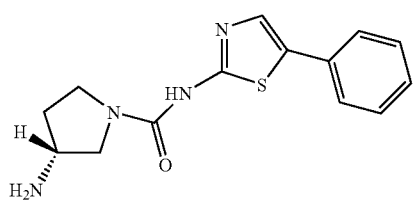

10

In a manner identical to that described above in Scheme 2, from 400 mg (1.17 mmol) of 2-(4-nitrophenoxycarbonyl) amino-5-phenylthiazole and 256 mg (1.17 mmol) of 3-(R)-trifluoroacetamido-pyrrolidine was obtained the crude trifluoroacetylated product. The product was dissolved in 3 mL methanol/1 mL DME/3 mL saturated aqueous K$_2$CO$_3$ and stirred at 50° C. for 3 hours. The reaction was cooled, acidified to pH 7 with 1N KHSO$_4$, diluted with ethyl acetate and stirred. The mixture was then filtered and the layers separated. The aqueous layer was re-extracted with ethyl acetate. The combined ethyl acetate extracts were dried and concentrated in vacuo to give a yellow oil. The oil was purified by reversed phase preparatory LC to give the TFA salt of 10 as a fluffy white amorphous solid. $H^1$ NMR (DMSO-d6): 2.00 (br m, 1H), 2.24 (br m, 1H), 3.56 (m, 3H), 3.87 (br m, 1H), 7.28 (t, 1H), 7.40 (t, 2H), 7.57 (d, 2H), 7.79 (s, 1H), 8.05 (br d, 2H). High Res. FAB MS: Theo. Mass=289.1118; measured mass=289.1126.

Example 11

Scheme 11: Synthesis of N-(5-phenylthiazol-2-yl)-N'-[4-(morpholin-1-yl)piperidin-1-yl)]urea (11-4)

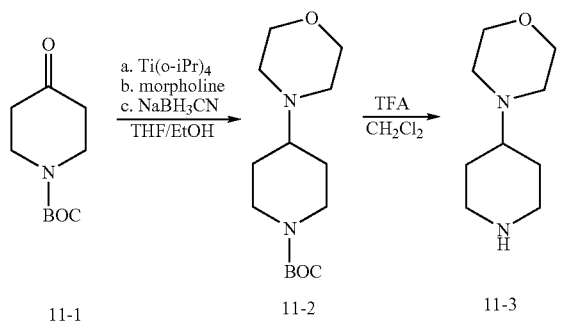

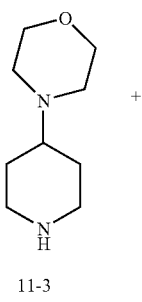

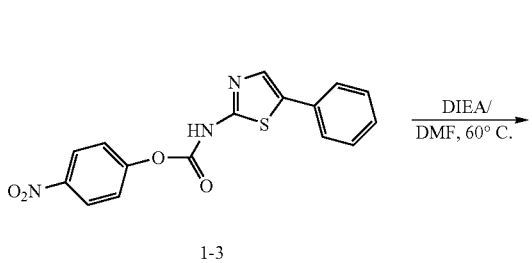

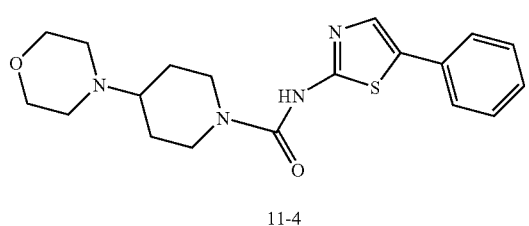

4-(morpholin-1-yl)-piperazine (11-3)

A mixture of 500 mg (2.51 mmol) of N-Boc-4-piperidinone 11-1, 219 μl (2.51 mmol) of morpholine, and 741 μl (2.51 mmol) of titanium isopropoxide was stirred for 1 hour in a nitrogen atmosphere. The reaction was diluted with 2 mL of absolute ethanol, and 126 mg (2.00 mmol) of sodium cyanoborohydride was added. The resulting mixture was stirred at room temperature for 18 hours. The reaction was diluted with 2 mL of water and filtered through a Celite pad. The filtrate was concentrated in vacuo and dissolved in ethyl acetate. The suspension was refiltered through Celite, and the filtrate concentrated in vacuo to a yellow oil. The oil was purified by reversed phase prep LC to yield 11-2 as a fluffy white amorphous powder after lyophilization. The powder was dissolved in 2 mL methylene chloride/2 mL TFA and stirred at room temperature for 18 hours. The reaction was concentrated in vacuo to afford amine 11-3 as a waxy solid.

N-(5-phenylthiazol-2-yl)-N'-[4-(morpholin-1-yl) piperidin-1-yl)]urea (11-4)

In a manner identical to that described above in Scheme 2, 338 mg (0.99 mmol) of 2-(4-nitrophenoxycarbonyl) amino-5-phenylthiazole 1-3 and 395 mg (0.99 mmol) of the bis TFA salt of 4-(morpholin-1-yl)-piperazine 11-3 were used to produce the TFA salt of 11-4 as a fluffy white amorphous solid after lyophilization. $H^1$ NMR (DMSO-d6): 1.53 (dq, 2H), 2.15 2.15 (dd, 2H), 2.85 (t, 2H), 3.12 (t, 1H), 3.46 (d, 4H), 3.67 (t, 2H), 4.02 (dd, 2H), 4.40 (br d, 1H), 7.27 (t, 1H), 7.40 (t, 2H), 7.56 (t, 2H), 7.77 (s, 1H), 9.70 (br s, 1H). High Res. FAB MS: Theo. Mass=373.1693; measured mass=373.1697

Example 12

N-(5-phenylthiazol-2-yl)-N'-[4-(pyrrolidinocarbonyl-methyl)piperazin-1-yl]-urea (12)

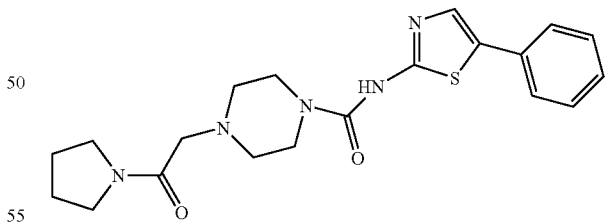

In a manner identical to that described above in Scheme 2, from 200 mg (0.59 mmol) of 2-(4-nitrophenoxycarbonyl) amino-5-phenylthiazole and 117 mg (0.59 mmol) of 1-(pyrrolidinocarbonylmethyl)piperazine was obtained 12 as an amorphous white powder after lyophilization. $H^1$ NMR (DMSO-d6): 1.82 (m, 2H), 1.94 (m, 2H), 3.13 (br m, 2H), 3.38 (complex, 6H), 3.52 (br m, 2H), 4.34 (br m, 2H), 7.28 (t, 1H), 7.41 (t, 2H), 7.56 (t, 2H), 7.78 (s, 1H), 10.14 (br s, 1H). High Res. FAB MS: Theo. Mass=400.1802; measured mass=400.1794.

Example 13

N-(5-phenylthiazol-2-yl)-N'-(3-carboxyazetidin-1-yl) urea (13)

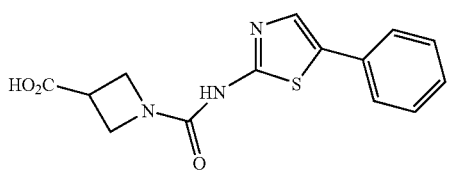

13

In a manner identical to that described above in Scheme 2, from 300 mg (0.90 mmol) of 2-(4-nitrophenoxycarbonyl) amino-5-phenylthiazole and 90 mg (0.9 mmol) of 4-carboxyazetidine was obtained 13 as an amorphous white powder after lyophilization. $H^1$ NMR (DMSO-d6): 3.43 (m, 1H), 4.06 (t, 2H), 4.20 (t, 2H), 7.27 (t, 1H), 7.39 (t, 2H), 7.56 (d, 2H), 7.77 (s, 1H). High Res. FAB MS: Theo. Mass=304.0750; measured mass=304.0741.

Example 14

N-(5-phenylthiazol-2-yl)-N'-[3-(R,S)-aminopiperidin-1-yl]urea (14)

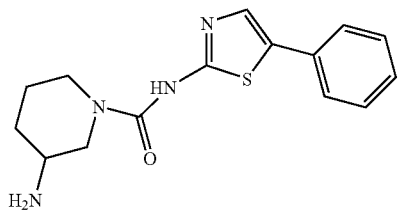

14

In a manner identical to that described above in Scheme 2 above, 250 mg (0.73 mmol) of 2-(4-nitrophenoxycarbonyl)amino-5-phenylthiazole and 227 mg (0.73 mmol) of the TFA salt of 3-(R,S)-trifluoroacetylaminopiperidine was obtained the crude trifluoroacetylated product. The product was dissolved in 3 mL methanol/1 mL DME/3 mL saturated aqueous $K_2CO_3$, and stirred at 50° C. for 18 hours. The reaction was cooled and then concentrated in vacuo to remove volatile organic compounds. The suspension was extracted twice with chloroform. The combined extracts were then dried and concentrated in vacuo to give an oily solid. The crude product was purified by reverse phase preparatory LC to give the TFA salt of 14 as a fluffy white amorphous solid. $H^1$ NMR (DMSO-d6): 1.50 (m, 1H), 1.56 (m, 1H), 1.75 (m, 1H), 1.97 (m, 1H), 3.21 (complex, 3H), 3.82 (m, 1H), 4.04 (m, 1H), 7.28 (t, 1H), 7.40 (t, 2H), 7.56 (d, 2H), 7.78 (s, 1H), 7.97 (br d, 2H). High Res. FAB MS: Theo. Mass=303.1274; measured mass=303.1269.

Example 15

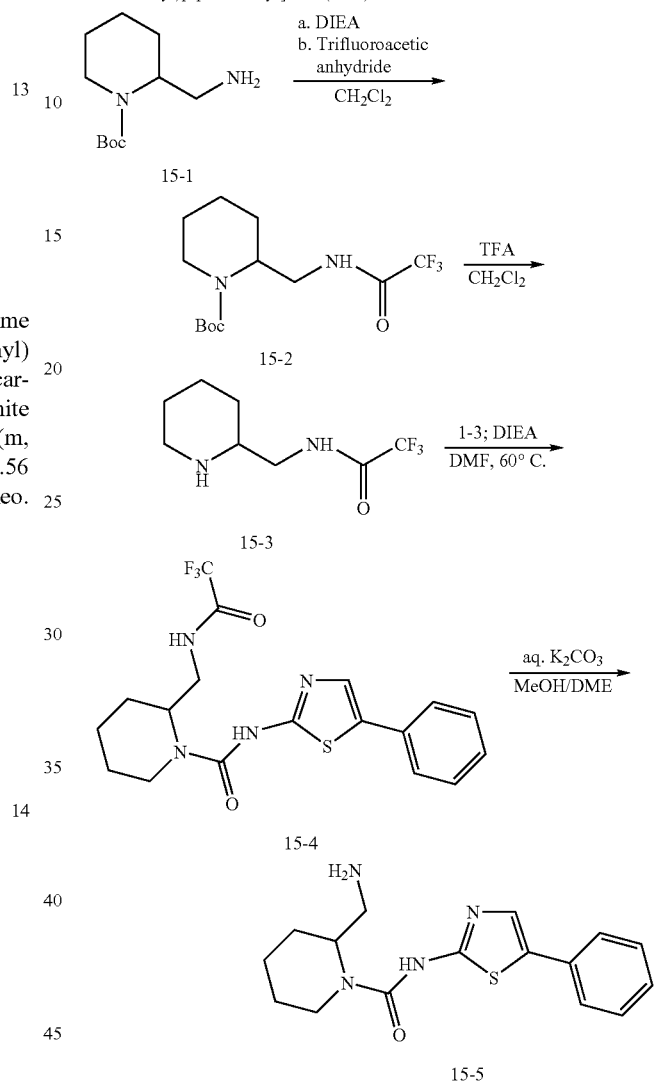

2-(R,S)-methyl(trifluoroacetylamino)piperidine (15-3)

A solution of 1.00 g (4.67 mmol) of 1-Boc-2-(methylamino)piperidine 15-1 and 660 µl (4.67 mmol) of DIEA in 10 mL of methylene chloride was cooled to 0° C. and treated dropwise with a solution of 814 µl (4.67 mmol) of trifluoroacetic anhydride in 1 mL of methylene chloride. The resulting solution was stirred at for 5 minutes and then warmed to room temperature for 2-3 hours. The reaction was washed with water, and the organic layer dried and concentrated to give 15-2 as a pale yellow solid. The solid was dissolved in 5 mL methylene chloride/5 mL TFA and stirred at room temperature for 1 hour. The reaction was concentrated in vacuo to afford the TFA salt of 15-3 as a tan oil-solid.

N-(5-phenylthiazol-2-yl)-N'-[2-(R,S-aminomethyl) piperidin-1-yl]urea (15-5)

Using the procedure described above in Example 2, 200 mg (0.59 mmol) of 2-(4-nitrophenoxycarbonyl)amino-5-phenylthiazole 1-3 and 192 mg (0.59 mmol) of the TFA salt of 2-(R,S)-methyl(trifluoroacetylamino)piperidine 15-3 were used to make the trifluoroacetylated product 15-4. The crude product was dissolved in 2 mL methanol/1 mL DME/2 mL saturated aqueous $K_2CO_3$, and stirred at 60° C. for 18 hours. The reaction was cooled and concentrated in vacuo to remove volatile organic compounds. The suspension was then extracted twice with ethyl acetate, and the combined extracts dried and concentrated in vacuo to give a yellow solid. This crude product was purified by reverse phase preparatory LC to give the TFA salt of 15-5 as a fluffy white amorphous solid. $H^1$ NMR (DMSO-d6): 1.39 (m, 1H), 1.59 (m, 4H), 1.68 (m, 1H), 2.96 (m, 2H), 3.32 (m, 2H), 4.61 (m, 1H), 7.28 (t, 1H), 7.40 (t, 2H), 7.56 (t, 2H), 7.77 (br, 2H), 7.79 (s, 1H). High Res. FAB MS: Theo. Mass=317.1431; measured mass=317.1427.

Example 16

Scheme 16: Synthesis of N-(5-phenylthiazol-2-yl)-N', N'-[4-(R, S)-aminohexahydroazepine-1-yl]urea (16-8)

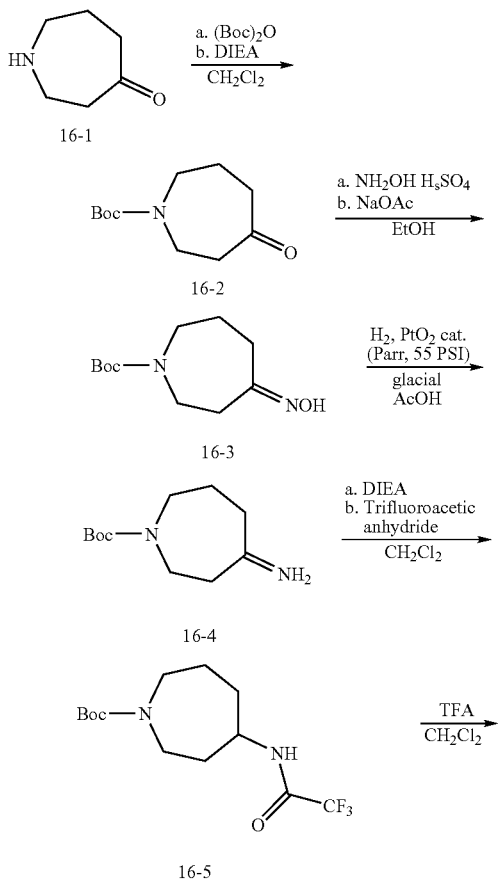

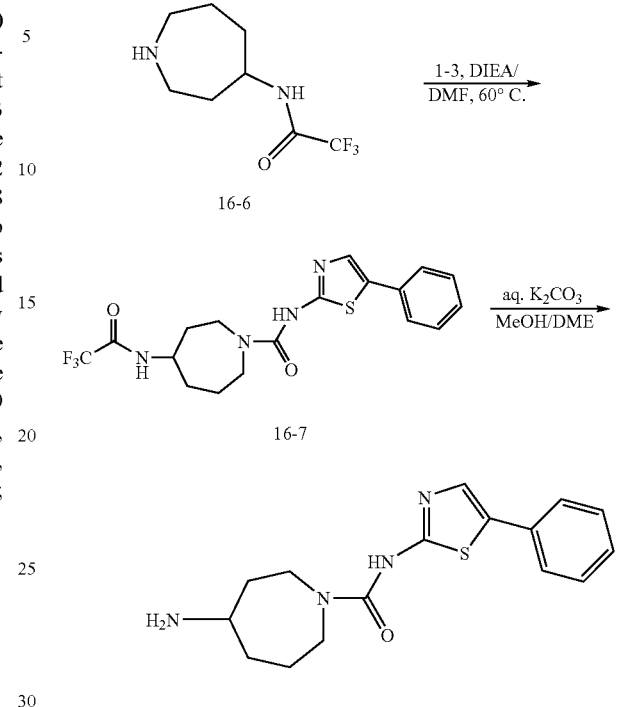

A solution of 720 mg (4.81 mmol) of hexahydro-4H-azepin-4-one hydrochloride 16-1 and 1.74 mL (10.00 mmol) of DIEA in 10 mL methylene chloride was cooled to 0° C. and treated portion wise with 1.16 g (5.21 mmol) of Boc anhydride over 5 minutes. After stirring at 0° C. for 5 minutes, the mixture was warmed to room temperature for 18 hours. The reaction was then washed with 5% aqueous acetic acid, washed with saturated aqueous $NaHCO_3$ solution, dried and concentrated to afford 16-2 as a clear oil.

A mixture of 800 mg (3.75 mmol) of 16-2, 770 mg (4.69 mmol) of hydroxylamine sulfate, 385 mg (4.69 mmol) of sodium acetate and 5 mL absolute ethanol was heated at 80° C. for 18 hours. The reaction was cooled and concentrated in vacuo. The residue was then partitioned between water and chloroform. The chloroform layer was dried and concentrated in vacuo to give oxime 16-3.

The oxime product from above, 16-3, was dissolved in 5 mL of glacial acetic acid and hydrogenated on a Parr apparatus over 120 mg of $PtO_2$ at 55 psi for 18 hours. The reaction was then filtered and the filtrate concentrated in vacuo to afford 16-4.

A solution of of 600 mg (2.80 mmol) of azepine 16-4 and 610 µl (3.50 mmol) of DIEA in 6 mL of methylene chloride was cooled to 0° C. and treated dropwise with a solution of 396 µl (2.80 mmol) of trifluoroacetic anhydride in 1 mL methylene chloride. The solution was stirred at 0° C. for 15 minutes and then warmed to room temperature for 2 hours. The reaction was concentrated in vacuo, and the residue partitioned between water and chloroform. The chloroform layer was washed with water, dried, and concentrated in vacuo to a clear oil. The oil was dissolved in 2 mL methylene chloride/2 mL TFA, and the solution stirred at room temperature for 2 hours. The mixture was then concentrated in vacuo to provide the TFA salt of 4-[(R,S)-trifluoroacetylamino]hexahydroazepine 16-5 as a clear oil.

Using the procedure described above in Example 2, 208 mg (0.61 mmol) of 2-(4-nitrophenoxycarbonyl)amino-5-phenylthiazole 1-3 and 198 mg (0.61 mmol) of the TFA salt of 16-5 were used to obtain the crude trifluoroacetylated product. The crude material was dissolved in 1 mL methanol/0.5 mL DME/1 mL saturated aqueous $K_2CO_3$, and stirred at 60° C. for 18 hours. The reaction was then cooled and concentrated in vacuo to remove volatile organics. The resulting suspension was extracted twice with ethylacetate, and the combined extracts dried and concentrated in vacuo to give an oily solid. This crude product was then purified by reverse phase preparatory LC to give yield the TFA salt of 16-8 as a fluffy white amorphous solid. $H^1$NMR (DMSO-d6): 1.55 (q, 1H), 1.72 (m, 2H), 1.96 (dd, 2H), 2.14 (m, 1H), 3.23 (m, 1H), 3.41 (br t, 1H), 3.61 (m, 2H), 3.89 (m, 1H), 7.34 (t, 1H), 7.46 (t, 2H), 7.74 (d, 2H), 7.84 (s, 1H), 7.87 (br, 2H). FAB MS: M+1=317.

Example 17

Scheme 17: Synthesis of 2-(4-nitrophenoxycarbonyl)aminothiazole (17-3)

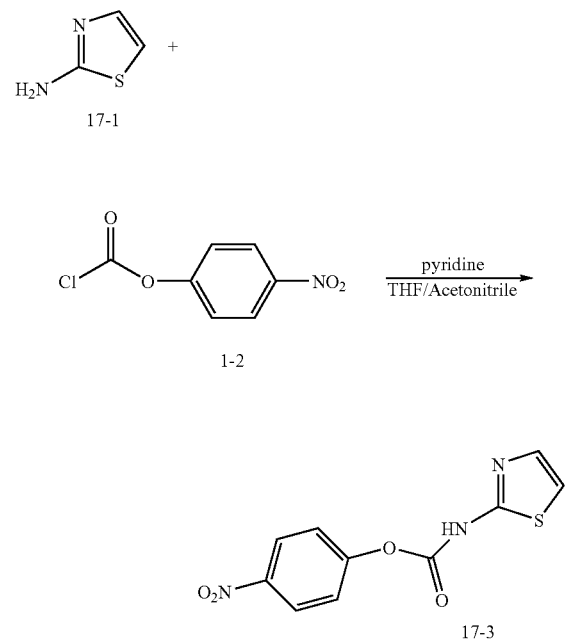

To a solution of 3.87 g (38.60 mmol) of 2-aminothiazole 17-1 in 48 mL of 7:1 THF/acetonitrile was added 7.78 g (38.60 mmol) of p-nitrophenylchloroformate 1-2, followed by 3.12 mL (38.60 mmol) of pyridine. A thick tan precipitate formed immediately. The resulting suspension was stirred vigorously at room temperature for 18 hours and then filtered. The tan solid precipitate was washed several times with portions of THF and dried in vacuo. The crude solid was heated with a heat gun in vacuo, and a small amount of a white volatile solid impurity was observed subliming off. After complete removal of the subliming solid, the product was left under vacuo for 18 hours to give 17-3 as a solid which was used without further purification.

Example 18

Scheme 18: Synthese of N-(5-Bromothiazol-2-yl)-N'-(4-aminopiperdin-1-yl)urea (18-4)

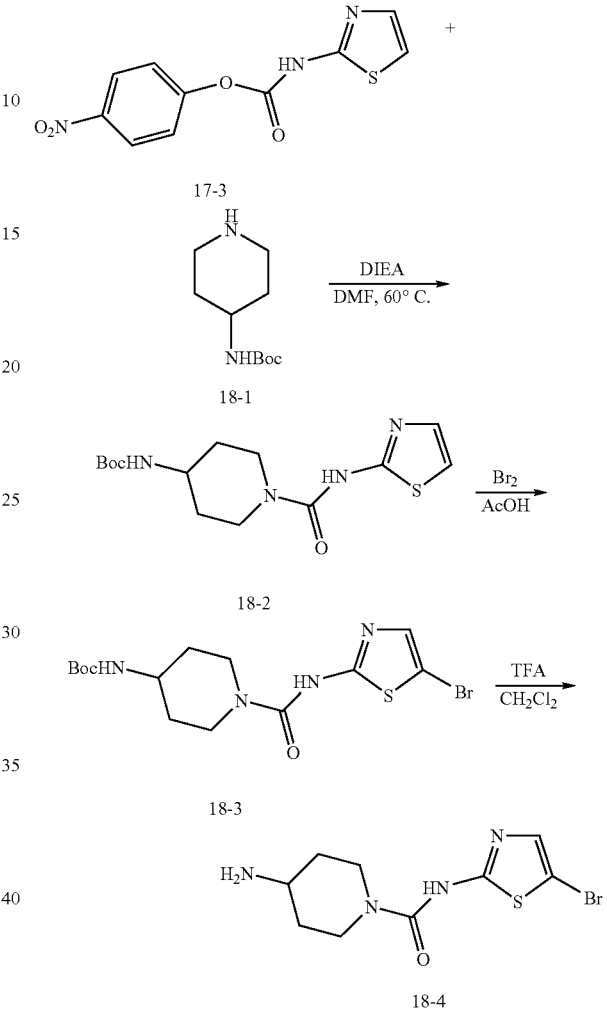

As described above in Scheme 2, 1.25 g (4.71 mmol) of 2-(4-nitrophenoxycarbonyl)aminothiazole 17-3 and 0.94 g (4.71 mmol mmol) of 4-Boc-amino-piperidine 18-1 were used to produce the Boc-protected product 18-2, which was used without further purification.

1.00 g (3.06 mmol) of 18-2 was dissolved in 5 mL of glacial acetic acid and treated dropwise with 0.50 g (3.06 mmol) of bromine. The resulting solution was stirred at room temperature for 2 hours and then concentrated in vacuo to produce an orange foam. The foam was purified by gravity column chromatography over silica gel with 49:1 chloroform/methanol to afford the Boc-protected 5-bomothiazole 18-3 as a yellow semi-solid.

100 mg of 18-3 was dissolved in 2 mL methylene chloride/2 mL TFA, and stirred at room temperature for 2 hours. The reaction was concentrated in vacuo to give an oil which was purified via reverse phase prep LC. Pure fractions provided the desired final product 18-4 as an amorphous white powder after lyophilization. $H^1$ NMR (DMSO-d6): 1.40 (dq, 2H), 1.90 (dd, 2H), 2.92 (t, 2H), 3.27 (m, 1H), 4.19 (dd, 2H), 7.47 (s, 1H), 7.92 (br, 2H). FAB MS: M+1=306.

Example 19

Scheme 19: Synthese of 4-amino-N-{5-[3-trifluoromethoxy)phenyl]-1,3-thiazol-2-yl}piperdine-1-carboxamide (19-15)

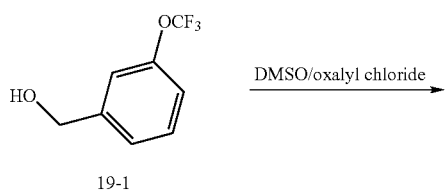

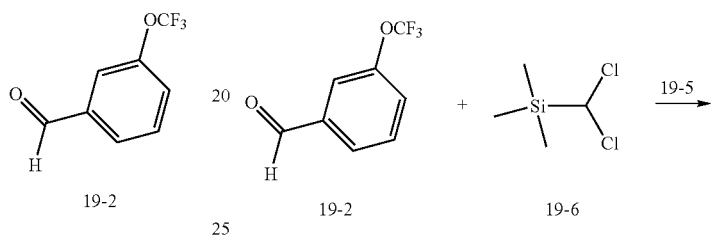

In a 100 mL 3-neck round-bottom flask was dissolved oxalyl chloride (0.53 g, 4.16 mmol) in a total of 15 mL of dichloromethane (DCM) under $N_2$. The solution was then cooled to −78° C. and dimethyl sulfoxide (0.41 g, 5.20 mmol) added slowly. After 10 minutes, 3-trifluoromethoxy-benzyl alcohol (0.5 g, 2.60 mmol) was added as a DCM solution (5 mL) keeping the temperature below −65° C. The reaction was stirred for an additional 30 minutes at −78° C. and then triethylamine (0.90 g, 8.85 mmol) was added via addition funnel over 3 minutes. This heterogenous mixture was stirred at −78° C. for 10 minutes and then removed from the dry ice bath. This was transferred to a separatory funnel, diluted with DCM, washed with water, aqueous $KHSO_4$, aqueous $NaHCO_3$, brine and dried with $Na_2SO_4$. Filtration and evaporation afforded 19-2. $H^1NMR$ ($CDCl_3$): 10.03 ppm (s, 1H); 7.83 ppm (d, 1H); 7.74 ppm (s, 1H); 7.59 ppm (t, 1H); 7.50 ppm (m, 1H).

Tris(diethylamino)sulfonium
Difluoro(trimethyl)silicate(1-) (19-5)

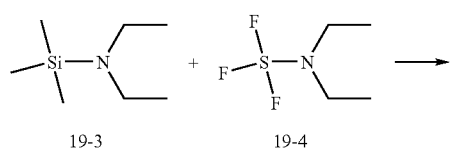

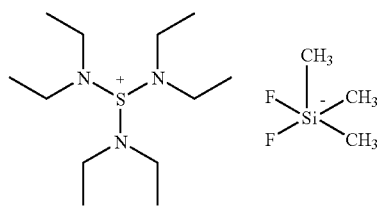

The title compound was prepared as outlined in Chem Abstracts, 1976, 85, 6388j as follows: [Diethylamino]trimethylsilane (1.53 g, 10.53 mmol) in 2 mL of ether was added to a cooled ether solution (2 mL) of [diethylamino]sulfur trifluoride (0.629 g, 3.90 mmol) via addition funnel. After the addition was complete the ice bath was removed and the solution was stirred for 18 hours at room temperature. The ether was evaporated off and the solid residue was dissolved in dry THF to make a 1M solution (3.67 mL).

2,2-Dichloro-1-[3-(trifluoromethoxy)phenyl]ethanol
(19-7)

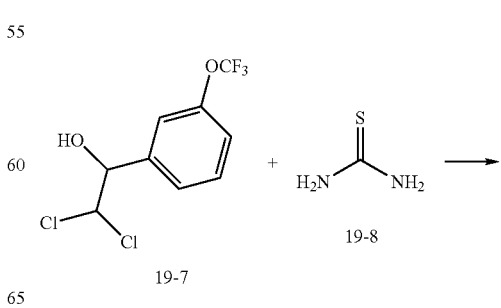

The title compound was prepared as outlined in JACS, 1985, 107, 4085-4087 as follows. A 1.0M THF solution of 19-2 (0.19 g, 1.0 mmol) was added to a THF solution (2 mL) of (dichloromethyl) trimethylsilane 19-6 (0.188 g, 1.2 mmol) and 19-5 (0.9 g, 0.25 mmol) and stirred at room temperature for 18 hours. The reaction was then treated with 300 μL (0.3 mmol) of 1N HCl/MeOH for 20 minutes and diluted with ethyl ether and water. The ether was removed, dried with sodium sulfate, filtered and evaporated to afford a 4:1 mixture of 19-7 and 3-(trifluoromethoxy)benzaldehyde. This was used without further purification.

5-[3-(Trifluoromethoxy)phenyl]-1,3-thiazol-2-amine
(19-9)

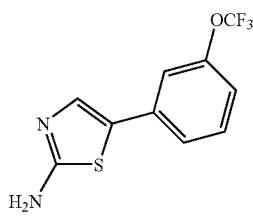

19-9

19-7 (0.182 g, 0.662 mmol) and thiourea (0.050 g, 0.662 mmol) were dissolved in methanol. Solid potassium hydroxide (0.037 g, 0.662 mmol) was then added and warmed to 50° C. while stirring under $N_2$. Additional solid potassium hydroxide pellets were added until the reaction was complete. The reaction was then directly loaded onto a $C_{18}$ preparative HPLC column. The titled compound was isolated upon evaporation. $H^1$ NMR (DMSO): 7.75 ppm (s, 1H); 7.51 ppm (m, 3H); 7.26 ppm (d, 2H).

4-Nitrophenyl 5-[3-(trifluoromethoxy)phenyl]-1,3-thiazol-2-yl-carbamate (19-12)

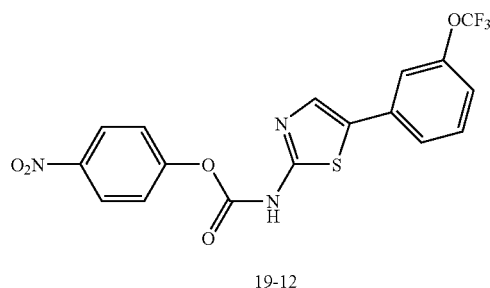

5-[3-(Trifluoromethoxy)phenyl]-1,3-thiazol-2-amine 19-9 (0.03 g, 0.08 mmol) was dissolved in 2 mL of THF/ACN (7:1) and to this was added a THF/ACN (7:1) solution (300 uL) of p-nitrophenylchloroformate 1-2 (0.018 g, 0.088 mmol). This was stirred for 15 minutes at 25° C. and then neat pyridine (0.014 g, 0.176 mmol) was added followed by stirring at 25° C. for 18 hours. The reaction was diluted with ethyl acetate and water. The organic layer was removed, dried, filtered and evaporated to yield crude 19-12.

Tert-butyl 1-[({5-[3-(trifluoromethoxy)phenyl]-1,3-thiazol-2-yl}amino)carbonyl]-4-piperidinylcarbamate (19-14)

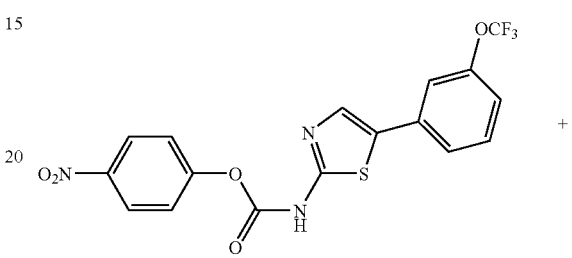

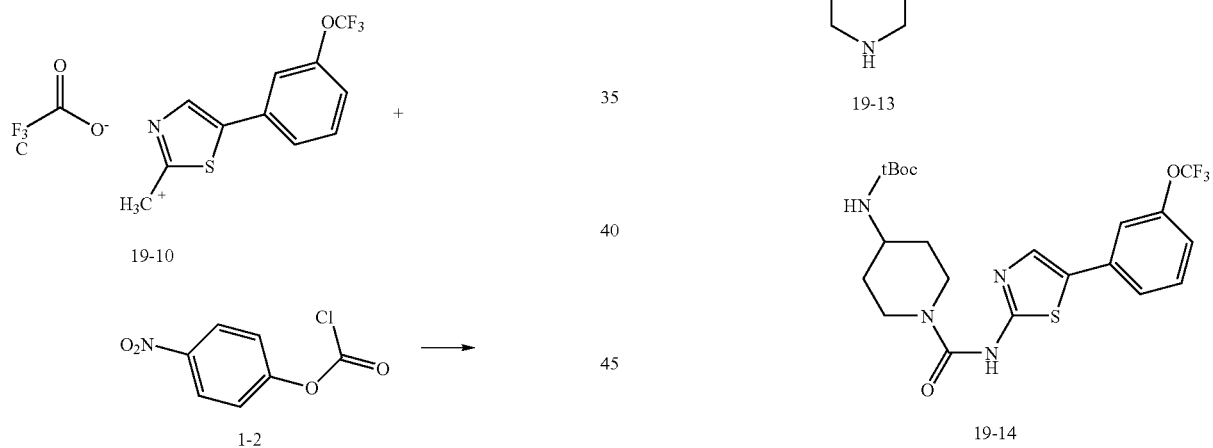

4-Nitrophenyl 5-[3-(trifluoromethoxy)phenyl]-1,3-thiazol-2-yl-carbamate 19-12 (0.072 g, 0.169 mmol) was dissolved in DMF (2 mL) and 4-boc-amino-1-piperidine 19-13 (0.034 g, 0.169 mmol) was added followed by DIEA (0.022 g, 0.169 mmol). The solution was stirred at 60° C. under $N_2$ and the reaction was complete in 1 hour. Most of the DMF was evaporated off and the residue was partitioned with ethyl acetate and dilute $NH_4OH$. The organic layer was washed repeatedly with dilute $NH_4OH$ until all the yellow color was gone. The organic layer was then dried, evaporated and the residue purified on a silica column eluted with DCM:MeOH (99:1 to 98:2) to afford 19-14. $^1$H-NMR (CDCl$_3$): 7.52 ppm (s, 1H); 7.40 ppm (m, 2H); 7.36 ppm (s, 1H); 7.13 ppm (d, 1H); 4.50 ppm (s, 1H); 4.12 ppm (d, 2H); 3.65 ppm (s, 1H); 3.08 ppm (t, 2H); 2.03 ppm (d, 2H); 1.75 ppm (s, 1H); 1.45 ppm (s, 9H).

4-Amino-N-{5-[3-(trifluoromethoxy)phenyl]-1,3-thiazol-2-yl}-1-piperidinecarboxamide (19-15)

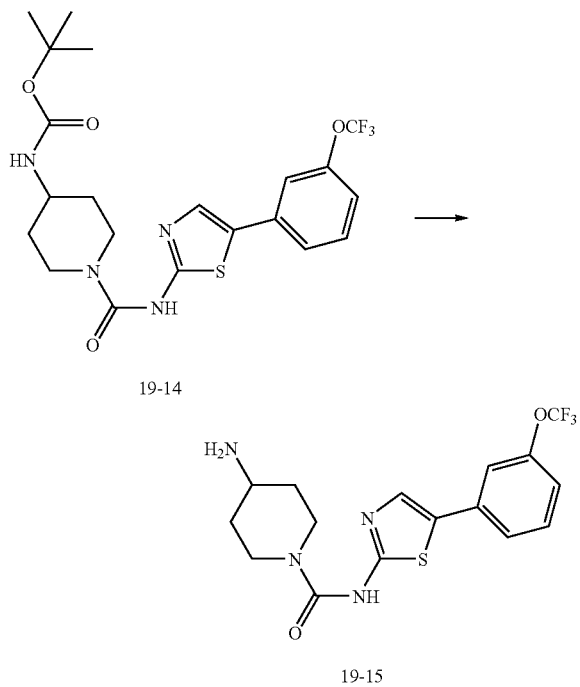

19-14

19-15

Tert-butyl 1-[({-5-[3-(trifluoromethoxy)phenyl]-1,3-thiazol-2-yl}amino)carbonyl]-4-piperidinylcarbamate 19-14 (0.016 g, 0.033 mmol) was dissolved in trifluoroacetic acid and stirred at room temperature until deblocking was complete. The trifluoroacetic acid was then removed under reduced pressure and the titled product 19-15 was isolated via lyophilization. Hi-Res MS: calc: 387.1097 found: 387.1092. $^1$H-NMR (DMSO): 7.94 ppm (s, 1H); 7.56 ppm (m, 3H); 7.26 ppm (d, 1H); 4.23 ppm (s, 2H); 3.27 ppm (s, 1H); 2.92 ppm (t, 2H); 1.91 ppm (d, 2H); 1.41 ppm (q, 2H).

Example 20

4-amino-N-[5-(3-cyanophenyl)-1,3-thiazol-2-yl]piperidine-1-carboxamide (20)

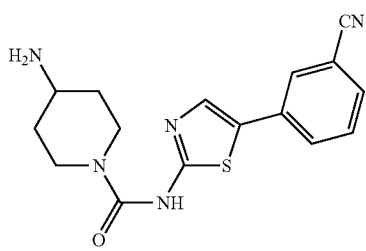

The titled compound was prepared as in Scheme 19 above replacing 3-(trifluoromethoxy)benzaldehyde with 3-cyanobenzaldehyde. Hi-Res MS: calc: 328.1227 found: 328.1248. $^1$H-NMR (DMSO): 8.03 ppm (s, 1H); 7.97 ppm (s, 1H); 7.85 ppm (d, 1H); 7.71 ppm (d, 1H); 7.59 ppm (t, 1H); 4.23 ppm (d, 2H); 3.24 ppm (m, 1H); 2.93 ppm (t, 2H); 1.91 ppm (d, 2H); 1.41 ppm (q, 2H).

Example 21

Scheme 21: Synthesis of 2,2,5,5-Tetramethyl-N-1-(5-phenyl-1,3-thiazol-2-yl)pyrrolidine-1,3-dicarboxamide (21-2)

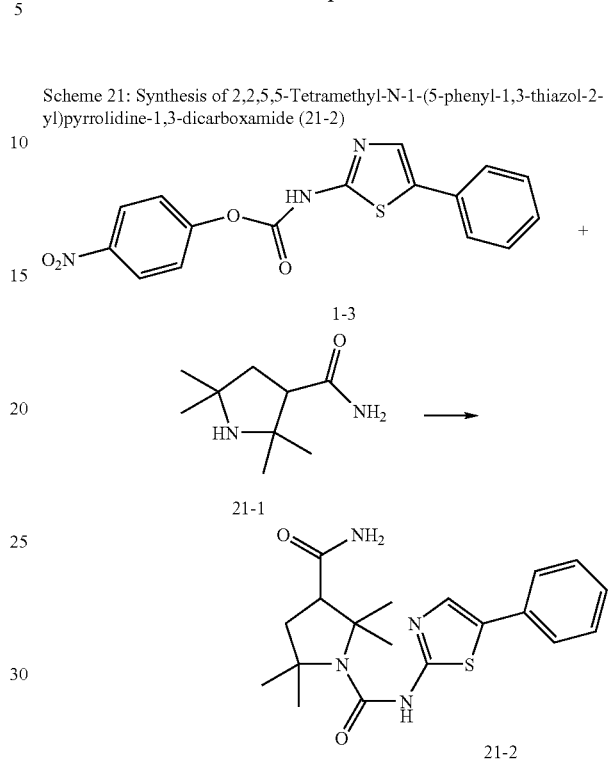

1-3

21-1

21-2

The titled compound was prepared by adding solid 4-nitrophenyl 5-phenyl-1,3-thiazol-2-ylcarbamate 1-3 (0.20 g, 0.586 mmol) to a DMF (3 mL) solution of 2,2,5,5-tetramethylpyrrolidine-3-carboxamide 21-1 (0.11 g, 0.645 mmol) and DIEA (0.227 g, 1.76 mmol). This was stirred for 18 hours at 25° C. The solution was diluted with ethyl acetate and brine and then transferred to a separatory funnel. The organic layer was exhaustively extracted with dilute ammonium hydroxide, dried, evaporated and then purified on a $C_{18}$ preparative HPLC column. The product, 21-2, was isolated via lyophilization. Hi-Res MS: calc: 373.1693 found: 373.1704. $^1$H-NMR (DMSO): 7.63 ppm (s, 1H); 7.53 ppm (d, 2H); 7.38 ppm (t, 2H); 7.32 ppm (s, 1H); 7.26 ppm (t, 1H); 7.00 ppm (s, 1H); 2.72 ppm (m, 1H); 2.13 ppm (t, 1H); 1.68 ppm (m, 4H); 1.53 ppm (m, 3H); 1.41 ppm (m, 3H); 1.27 ppm (m, 3H).

Example 22

Scheme 22: Synthesis of (2S,5S)-2,5-bis(methoxymethyl)-N-(5-phenyl-1,3-thiazol-2-yl)pyrrolidine-1-carboxamide (22-2)

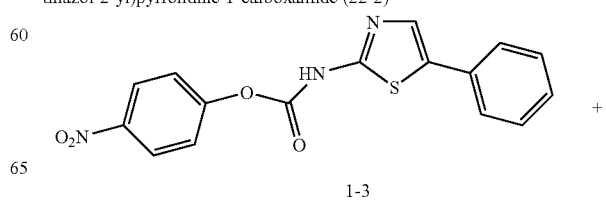

1-3

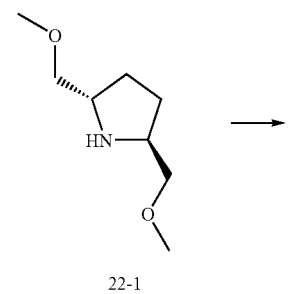

22-1

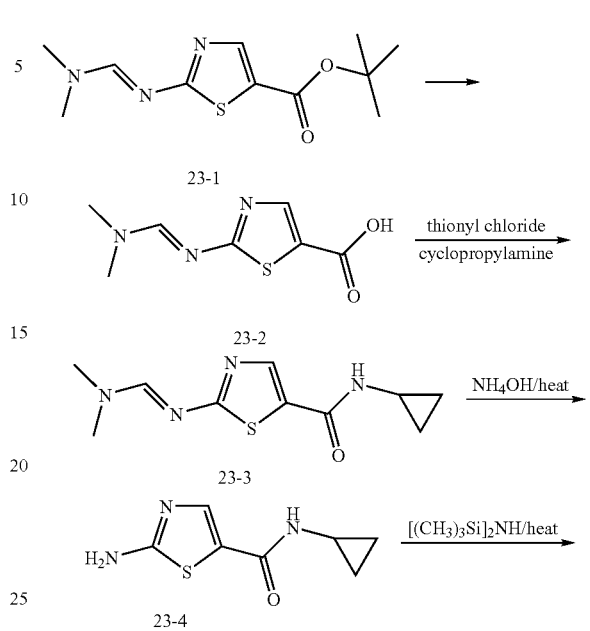

The titled compound was prepared as in Scheme 21 above replacing 2,2,5,5-tetramethylpyrrolidine-3-carboxamide with (2S, 5S)-2,5-bis(methoxymethyl) pyrrolidine 22-1. Hi-Res MS: calc: 362.1533 found: 362.1517. $^1$H-NMR (DMSO): 7.75 ppm (s, 1H); 7.56 ppm (s, 2H); 7.40 ppm (t, 2H); 7.27 ppm (t, 1H); 4.10 ppm (m, 2H); 3.44 ppm (m, 2H); 3.27 ppm (s, 8H); 2.04 ppm (m, 2H); 1.78 ppm (m, 2H).

Example 23

Scheme 23:Synthesis of 4-amino-N-{5-[cyclopropylamino)carbonyl]-1,3-thiazol-2-yl}piperidine-1-carboxamide (23-7)

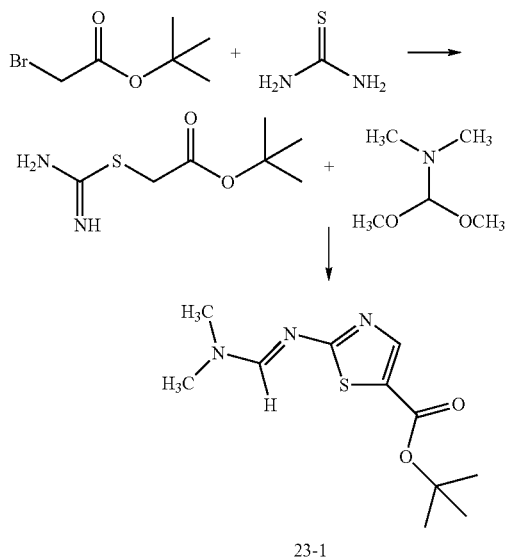

Tert-butyl 2-{[(1E)-(dimethylamino)methylidene]amino}-1,3-thiazole-5-carboxylate (23-1)

tert-Butyl bromoacetate (19.5 g, 100 mmol) and thiourea (7.6 g, 100 mmol) were combined in 100 mL of dioxane and heated to near reflux for 20 minutes. Upon cooling a precipitate formed which was air dried and mixed with dimethylformamide acetal (47.6 g, 400 mmol). After stirring at room temperature for 18 hours, the reaction was concentrated and partitioned between ethyl acetate and water. The organic was drawn off, washed with brine, dried with sodium sulfate and concentrated to a solid. $^1$H-NMR (CDCl$_3$): 8.3 ppm (s, 1H); 7.9 ppm (s, 1H); 3.1 ppm (d, 6H); 1.5 ppm (s, 9H).

2-{[(1E)-(Dimethylamino)methylidene]amino}-1,3-thiazole-5-carboxylic acid (23-2)

To tert-butyl 2-{[(1E)-(dimethylamino)methylidene]amino}-1,3-thiazole-5-carboxylate 23-1 (12.3 g, 48.17 mmol) was added 35 mL of 4N HCl/dioxane. This suspension was warmed to 75° C. under nitrogen for 18 hours. The solid was filtered off, washed with dioxane and ethyl ether, and then dried under high vacuum at 45° C. $^1$H-NMR (DMSO): 8.57 ppm (s, 1H); 8.07 ppm (s, 1H); 3.26 ppm (s, 3H); 3.12 ppm (s, 3H).

N-cyclopropyl-2-{[(1E)-(dimethylamino)methylidene]amino}-1,3-thiazole-5-carboxamide (23-3)

To a 100 mL flask was charged 2-{[(1E)-(dimethylamino)methylidene]amino}-1,3-thiazole-5-carboxylic acid 23-2 (0.56 g, 2.37 mmol) and thionyl chloride (5 mL). This suspension was refluxed for 75 minutes. At the end of this time the homogeneous solution was evaporated to dryness and the residue was flushed 2 times with CCl$_4$. This residue was then dissolved in methylene chloride and triethylamine (1.20 g, 11.8 mmol) was added followed by cyclopropylamine (0.47 g, 8.29 mmol). The reaction was stirred overnight at 25° C. A precipitate was filtered off. Hi-Res MS: calc: 239.0961 found: 239.0959. $^1$H-NMR (DMSO): 8.36 ppm (s, 1H); 8.27 ppm (s, 1H); 7.83 ppm (s, 1H); 3.12 ppm (s, 3H); 2.98 ppm (s, 3H); 2.72 ppm (m, 1H); 0.67 ppm (m, 2H); 0.52 ppm (m, 2H).

2-Amino-N-cyclopropyl-1,3-thiazole-5-carboxamide (23-4)

N-cyclopropyl-2-{[(1E)-(dimethylamino)methylidene]amino}-1,3-thiazole-5-carboxamide 23-3 (1.01 g, 4.23 mmol) was heated to 75° C. in 20 mL of concentrated NH$_4$OH in a sealed tube. After 4 hours the hydrolysis was complete and most of the liquid was evaporated off. Additional water was then added and the pH adjusted to 6. The aqueous layer was extracted with ethyl acetate (4×) and all organics were combined, dried, evaporated and flushed with toluene (2×). $^1$H-NMR (DMSO): 8.06 ppm (s, 1H); 7.55 ppm (s, 1H); 7.42 ppm (s, 2H); 2.68 ppm (m, 1H); 0.64 ppm (m, 2H); 0.48 ppm (m, 2H).

N-Cyclopropyl-2-[(trimethylsilyl)amino]-1,3-thiazole-5-carboxamide (23-5)

2-Amino-N-cyclopropyl-1,3-thiazole-5-carboxamide 23-4 (0.18 g, 1.0 mmol) was boiled in 1 mL of 1,1,1,3,3,3-hexamethyldisilazane for 18 hours. The solvent was then removed under reduced pressure to afford the product. $^1$H-NMR (CDCl$_3$): 7.46 ppm (s, 1H); 2.82 ppm (m, 1H); 0.84 ppm (m, 2H); 0.61 ppm (m, 2H); 0.34 ppm (s, 9H).

4-Amino-N-{5-[(cyclopropylamino)carbonyl]-1,3-thiazol-2-yl}piperidine-1-carboxamide (23-7)

N-Cyclopropyl-2-[(trimethylsilyl)amino]-1,3-thiazole-5-carboxamide 23-5 (0.26 g, 1.0 mmol) was treated with 2 mL of phosgene (as a 20% solution in toluene) and 1 mL of methylene chloride at room temperature for 4 hours. The suspension was concentrated to dryness and the residue was treated with a suspension of DIEA (0.16 g, 1.2 mmol) and 4-boc-amino-1-piperidine 23-6 (0.20 g, 1.0 mmol) in 1 mL of dry DMF and 1 mL of methylene chloride overnight at room temperature. The intermediate product was purified on C$_{18}$ column and the residue treated with TFA. The crude product was purified on a C$_{18}$ preparative HPLC column and isolated via lyophilization to afford the final product 23-7. Hi-Res MS: calc: 310.1332 found: 310.1334. $^1$H-NMR (DMSO): 8.33 ppm (s, 1H); 7.92 ppm (s, 1H); 7.84 ppm (m, 3H); 3.27 ppm (m, 1H); 2.91 ppm (t, 2H); 2.75 ppm (m, 1H); 1.90 ppm (d, 2H); 1.40 ppm (q, 2H); 0.67 ppm (m, 2H); 0.52 ppm (m, 2H).

Example 24 tert-butyl 4-{[(5-phenyl-1,3-thiazol-2-yl)amino]carbonyl}-1,4-diazepane-1-carboxylate (24)

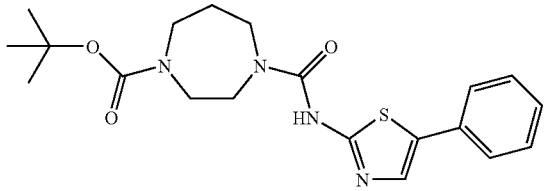

24

4-Nitrophenyl 5-phenyl-1,3-thiazol-2-ylcarbamate (200.0 mg, 0.59 mmol) along with tert-butyl 1,4-diazepene-1-carboxylate (125.0 ul, 0.64 mmol), diisopropylethylamine (205.5 ul, 2.1 mmol), and dimethylformamide (2.0 ml) were combined and heated at 60° C. overnight. The reaction was poured into brine (25 ml) containing ammoniumhydroxide (2.0 ml). The mixture was extracted with ethyl acetate (4×25 ml) and the ethylacetate layer back extracted with additional brine/ammonium hydroxide until the yellow color had faded. The ethylacetate layer was dried (MgSO$_4$), and the solvent removed to give tert-butyl 4-{[(5-phenyl-1,3-thiazol-2-yl)amino]carbonyl}-1,4-diazepane-1-carboxylate 24. $^1$H-NMR (500 MHz, CDCl$_3$): 9.30 (1H, br s), 7.53 (3H, m), 7.37 (2H, t, J=7.81 Hz), 7.28 (1H, t, J=7.08), 3.64 (2H, br s), 3.56 (4H, br s), 3.45 (1H, br s), 3.40 (1H, br s), 1.92 (2H, br s), 1.44 (9H, s). High res. ES MS: Theoretical Mass 403.1798, Measured Mass 403.1801 (C$_{20}$H$_{26}$N$_4$O$_3$S+H$^+$)

Example 25

4-{[(5-phenyl-1,3-thiazol-2-yl)amino]carbonyl}-1,4-diazepan-1-ium trifluoroacetate (25)

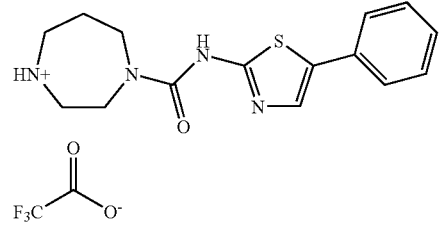

25 tert-butyl 4-{[(5-phenyl-1,3-thiazol-2-yl)amino]carbonyl}-1,4-diazepane-1-carboxylate (211.0 mg, 0.52 mmol) was treated with trifluoroacetic acid (2.0 ml) for fifteen minutes. The solvent was removed and the residue put under high vacuum to afford 4-{[(5-phenyl-1,3-thiazol-2-yl)amino]carbonyl}-1,4-diazepan-1-ium trifluoroacetate 25. $^1$H-NMR (500 MHz, DMSO-d$_6$): 8.73 (1H, br s), 8.68 (1H, br s) 7.78 (1H, s), 7.57 (2H, d, J=7.57), 7.40 (2H, t, J=7.57), 7.28 (1H, t, J=7.57), 3.76 (2H, br s), 3.63 (2H, br s), 3.21

(4H, br s), 1.98 (2H, br m). High res. ES MS: Theoretical Mass 303.1274, Measured Mass 303.1276($C_{15}H_{19}N_4OS+H^+$)

Example 26 tert-butyl (1-{[(5-phenyl-1,3-thiazol-2-yl)amino]carbonyl}piperidin-4-yl)methylcarbamate (26)

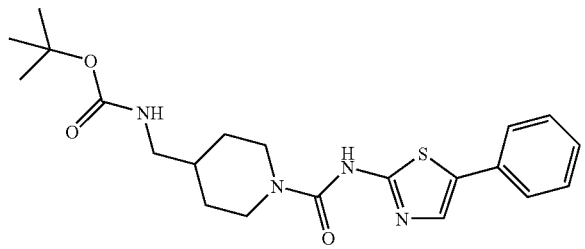

tert-Butyl (1-{[(5-phenyl-1,3-thiazol-2-yl)amino]carbonyl}piperidin-4-yl)methylcarbamate was prepared as in Example 24 above substituting tert-butyl piperidin-4-ylmethylcarbamate for tert-butyl 1,4-diazepane-1-carboxylate. $^1$H-NMR (500 MHz, CDCl$_3$): 7.48 (3H, m), 7.40 (2H, t, J=7.57 Hz), 7.35 (1H, t, J=7.32), 4.13 (2H, br s), 3.26 (2H, br s), 2.70 (2H, br s), 1.73 (3H, d, J=11.47), 1.46 (9H, s), 1.18 (2H, m). High res. ES MS: Theoretical Mass 417.1955, Measured Mass 417.1950 ($C_{21}H_{28}N_4O_3S+H^+$)

Example 27

(1-{[(5-phenyl-1,3-thiazol-2-yl)amino]carbonyl}piperidin-4-yl)methanaminium trifluoroacetate (27)

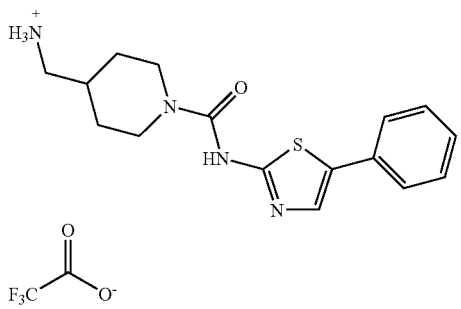

(1-{[(5-phenyl-1,3-thiazol-2-yl)amino]carbonyl}piperidin-4-yl)methanaminium trifluoroacetate 27 was prepared as Example 24 above. $^1$H-NMR (500 MHz, DMSO-d$_6$): 8.53 (1H, br s), 8.19 (1H, br s) 7.23 (1H, s), 7.55 (2H, d, J=8.06), 7.39 (2H, t, J=7.82), 7.27 (1H, t, J=7.33), 6.75 (1H, br s), 3.28 (2H, br d), 3.09 (2H, br m), 2.86(2H, br m), 1.78 (3H, br m), 1.30 (2H, br m). High res. ES MS: Theoretical Mass 317.1431, Measured Mass 317.1431 ($C_{16}H_{20}N_4OS+H^+$)

Example 28

4-carboxy-1-{[(5-phenyl-1,3-thiazol-2-yl)amino]carbonyl}piperidin-4-aminium trifluoroacetate (28)

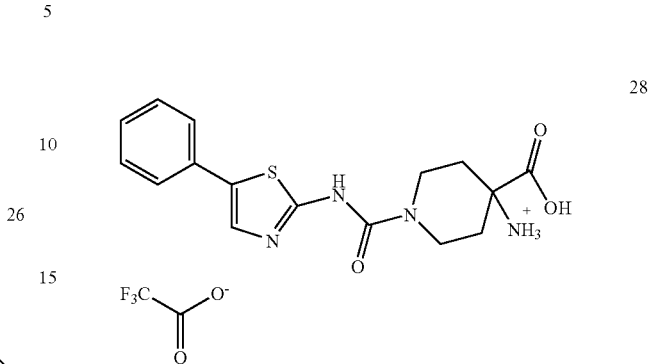

4-carboxy-1-{[(5-phenyl-1,3-thiazol-2-yl)amino]carbonyl}piperidin-4-aminium trifluoroacetate 28 was prepared as in Example 24 above substituting 4-ammonio-4-carboxypiperidinium dichloride for tert-butyl 1,4-diazepane-1-carboxylate. $^1$H-NMR (500 MHz, DMSO-d$_6$): 7.78 (1H, s), 7.56 (2H, d, J=7.57 Hz), 7.40 (2H, t, J=7.81 Hz), 7.28 (1H, t, J=7.33), 3.80 (2H, br s), 3.59 (2H, br s), 209 (2H, br m), 1.78 (2H, br m). High res. ES MS: Theoretical Mass 347.1172, Measured Mass 347.1161 ($C_{16}H_{18}N_4O_3S+H^+$).

What is claimed is:
1. A compound of Formula I

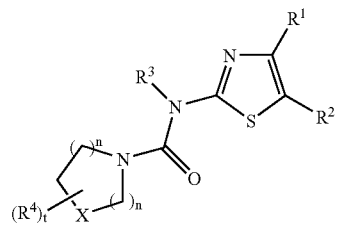

or a pharmaceutically acceptable salt or stereoisomer thereof, wherein
X is: C—H;
one n is 1 and one n is 2;
t is: 1 through 6;
$R^1$ is:
 1) H,
 2) halo,
 3) $C^{1-6}$ alkyl, or
 4) $OC^{1-6}$ alkyl;
$R^2$ is:
 1) aryl, optionally substituted with one to three substituents selected from:
  a) halo,
  b) $OC_{1-3}$ perfluoroalkyl,
  c) $OC_{1-6}$ alkyl,
  d) CN,
  e) OH,
  f) $SO_2R^d$,
  g) $C_{1-6}$ alkyl,
  h) i) (C=O)$R^d$, and
  i) $CO_2R^d$, 2) CN,
3) (C=O)NR$^a$R$^b$,
5) C$_{3-6}$ cycloalkyl, or
6) —C≡C—R$^c$;

R$^3$ is:
1) H,
2) C$_{1-8}$ alkyl,
3) SO$_2$R$^d$,
4) (C=O)R$^d$, or
5) CO$_2$R$^d$;

R$^{3a}$ is:
1) H,
2) SO$_2$R$^d$,
3) heterocyclyl,
4) (C=O)R$^d$,
5) CO$_2$R$^d$, or
6) C$_{1-8}$ alkyl, said alkyl is optionally substituted with one to three substituents selected from oxo, heterocyclyl, halo, NR$^5$R$^6$, CO$_2$H, CO$_2$R$^d$, CONR$^5$R$^6$, OH and OC$_{1-6}$ alkyl;

R$^4$ is:
1) H,
2) C$_{0-6}$ alkylene-NR$^5$R$^6$,
3) CO$_2$H,
4) CO$_2$R$^d$,
5) halo,
6) OH,
7) C$_{1-8}$ alkoxy, or
8) C$_{1-8}$ alkyl, said alkyl is optionally substituted with one to three substituents selected from oxo, heterocyclyl, halo, NR$^5$R$^6$, CO$_2$H, CO$_2$R$^d$, CONR$^5$R$^6$, OH and OC$_{1-6}$ alkyl;

R$^5$ and R$^6$ are independently:
1) H,
2) C$_{1-8}$ alkyl,
3) SO$_2$R$^d$,
4) CO$_2$R$^d$,
5) (C=O)R$^d$,
6) C$_{1-8}$ alkylene-NR$^a$R$^b$,
7) C$_{1-8}$ alkylene-(CO)NR$^a$R$^b$,
8) C$_{1-8}$ alkylene-heterocyclyl, or
9) aryl,
said aryl and heterocyclyl optionally substituted with one or more substituents selected from C$_{1-6}$ alkyl, C$_{1-3}$ perfluoroalkyl, C$_{1-6}$ alkoxy, OCF$_3$, SO$_2$R$^d$, NR$^a$R$^b$ and halo; or R$^5$ and R$^6$ are taken with the nitrogen to which they are attached to form a monocyclic or bicyclic heterocycle with 5-7 members in each ring, said heterocycle optionally substituted with one or more substituents selected from halo, C$_{1-6}$ alkyl, OC$_{1-6}$ alkyl, OCF$_3$, CO$_2$R$^d$, (C=O)R$^d$, aryl, heterocyclyl, SO$_2$R$^d$ and OH;

R$^a$ and R$^b$ are independently:
1) H,
2) C$_{1-6}$ alkyl,
3) C$_{3-6}$ cycloalkyl,
4) phenyl,
5) CO$_2$R$^d$,
6) (C=O)R$^d$, or
7) SO$_2$R$^d$;

R$^c$ is H, phenyl, or C$_{1-6}$ alkyl; and
R$^d$ is phenyl or C$_{1-6}$ alkyl.

2. The compound of claim 1, or a pharmaceutically acceptable salt or stereoisomer thereof, wherein R$^2$ is:
a) phenyl, optionally substituted with one or two substituents selected from:
1) halo,
2) OC$_{1-3}$ perfluoroalkyl,
3) OC$_{1-6}$ alkyl,
4) CN, and
5) C$_{1-6}$ alkyl,
b) CN, or
c) (C=O)NR$^a$R$^b$.

3. The compound of claim 2, or a pharmaceutically acceptable salt or stereoisomer thereof, wherein R$^1$, R$^3$, R$^4$ are H.

4. A compound selected from:
N-(5-phenylthiazol-2-yl)-N'-[4-(2-pyridyl)piperazin-1-yl]urea;
N-(5-phenylthiazol-2-yl)-N'-[4-(2-pyrimidinyl)piperazin-1-yl]urea;
N-(5-phenylthiazol-2-yl)-N'-(4-aminopiperidin-1-yl) urea;
N-(5-phenylthiazol-2-yl)-N'-[4-(2-pyrimidinoxy)piperidin-1-yl)]urea;
N-(5-phenylthiazol-2-yl)-N'-(4-carboxypiperidin-1-yl) urea;
N-(5-phenylthiazol-2-yl)-N'-(3-carboxyazetidin-1-yl) urea; and
N-(5-phenylthiazol-2-yl)-N'-[4-(pyrrolidinocarbonylmethyl) piperazine-1-yl]-urea; or a pharmaceutically acceptable salt or steroisomer thereof.

5. A pharmaceutical composition which is comprised of a compound in accordance with claim 1 and a pharmaceutically acceptable carrier.

* * * * *